United States Patent
Jiang et al.

(10) Patent No.: US 10,532,987 B2
(45) Date of Patent: Jan. 14, 2020

(54) COMPOUNDS AND METHODS FOR INDUCING BROWNING OF WHITE ADIPOSE TISSUE

(71) Applicant: GUANGZHOU INSTITUTES OF BIOMEDICINE AND HEALTH, CHINESE ACADEMY OF SCIENCES, Guangdong (CN)

(72) Inventors: Baishan Jiang, Guangdong (CN); Tao Nie, Guangdong (CN); Wenling Zhao, Guangdong (CN); Yali Zou, Guangdong (CN); Qiang Ding, Guangdong (CN); Sheng Ding, Guangdong (CN); Donghai Wu, Guangdong (CN)

(73) Assignee: GUANGZHOU INSTITUTES OF BIOMEDICINE AND HEALTH, CHINESE ACADEMY OF SCIENCE, Guangdong (CN)

( * ) Notice: Subject to any disclaimer, the term of this patent is extended or adjusted under 35 U.S.C. 154(b) by 0 days.

(21) Appl. No.: 15/551,509

(22) PCT Filed: Feb. 17, 2015

(86) PCT No.: PCT/CN2015/073223
§ 371 (c)(1),
(2) Date: Aug. 16, 2017

(87) PCT Pub. No.: WO2016/131192
PCT Pub. Date: Aug. 25, 2016

(65) Prior Publication Data
US 2018/0037556 A1 Feb. 8, 2018

(51) Int. Cl.
| C07D 417/12 | (2006.01) |
| C07D 277/42 | (2006.01) |
| C07D 277/82 | (2006.01) |
| C07D 277/46 | (2006.01) |
| C07D 417/14 | (2006.01) |

(52) U.S. Cl.
CPC ......... *C07D 277/46* (2013.01); *C07D 277/42* (2013.01); *C07D 277/82* (2013.01); *C07D 417/12* (2013.01); *C07D 417/14* (2013.01)

(58) Field of Classification Search
CPC .. C07D 417/12; C07D 277/42; C07D 277/82; C07D 277/46; C07D 417/14
See application file for complete search history.

(56) References Cited

U.S. PATENT DOCUMENTS

| 8,920,785 B2 | 12/2014 | Kolbe et al. |
| 2010/0316584 A1 | 12/2010 | Hanyu et al. |

FOREIGN PATENT DOCUMENTS

| CN | 101965177 A | 2/2011 |
| CN | 103179947 A | 6/2013 |
| JP | 2010533147 A | 10/2010 |
| JP | 2010540667 A | 12/2010 |
| JP | 2013-530927 A | 1/2013 |
| WO | 03/062215 A1 | 7/2003 |
| WO | 03062215 A1 | 7/2003 |
| WO | 2005/099673 A1 | 10/2005 |
| WO | 2005099673 A1 | 10/2005 |
| WO | 2007089512 A1 | 8/2007 |
| WO | 2009/099195 A1 | 8/2009 |
| WO | 2012/015715 A1 | 2/2012 |
| WO | 2012015715 A1 | 2/2012 |
| WO | 2013033037 A2 | 3/2013 |
| WO | 2013/033037 A2 | 7/2013 |

OTHER PUBLICATIONS

Joshi et al., 1962, caplus an 1962:429619.*
RN315705-34-1, date 2001.*
Gallardo-Godoy et al., 2011, caplus an 2011:84240.*
Thakar et al., 1978, caplus an 1978:597384.*
Ghaemmaghami et al., 2010, 84(7), 3408-3412.*
RN774543-84-9, 2004, registry database compound.*
International Search Report for PCT/CN2015/073223 dated Nov. 20, 2015.
Parameshwer Makam, et al., "2-Aminothiazole derivatives as antimycobacterial agents: Synthesis, characterization, in vitro and in silico studies," European Journal of Medicinal Chemistry, 87:643-656 (Sep. 30, 2014).
Sina Ghaemmaghami, et al., "Discovery of 2-Aminothiazoles as Potent Antiprion Compounds," Journal of Virology, 84:7:3408-3412 (Apr. 30, 2010).
Shridhar Bhat, et al., "Tricyclic thiazoles are a new class of angiogenesis inhibitors," Bioorganic & Medicinal Chemicstry Letters, 23:2733-2737 (2013).
Stn Columbus Registry. "RN: 1042853-24-6", Entered STN:, (Aug. 22, 2008).
STN Columbus Registry. "RN: 1171310-23-8," Entered STN:, (Jul. 31, 2009).
STN Columbus Registry. "RN: 380174-17-4," Entered STN:, (Jan. 2, 2002).
STN Columbus Registry. "RN: 497083-40-6," Entered STN:, (Mar. 6, 2003).
STN Columbus Registry. "RN: 327971-37-9," Entered STN:, (Mar. 19, 2001).

(Continued)

Primary Examiner — Sun Jae Yoo
(74) Attorney, Agent, or Firm — Abelman, Frayne & Schwab

(57) ABSTRACT

The present invention provides a compound for inducing browning of white adipose tissue in vitro and in vivo of formula I, the preparation method thereof, as well as a composition comprising the same. Further, the present invention also relates to the use of the compound and the method to treat metabolic disorders, such as obesity and diabetes.

(I)

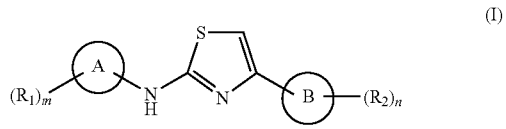

3 Claims, 1 Drawing Sheet

(56) References Cited

OTHER PUBLICATIONS

STN Columbus Registry. "RN: 1042868-31-4," Entered STN:, (Aug. 2, 2008).
STN Columbus Registry. "RN: 774543-84-9," Entered STN:, (Nov. 4, 2004).
STN Columbus Registry. "RN: 1324541-73-2," Entered STN:, (Aug. 28, 2011).
STN Columbus Registry, "RN: 315706-20-8," Entered STN:, (Jan. 22, 2001).
STN Columbus Registry. "RN: 700803-18-5," Entered STN:, (Jun. 28, 2004).
STN Columbus Registry. "RN: 1089559-86-3," Entered STN:, (Dec. 24, 2008).
STN Columbus Registry. "RN: 1030100-85-6," Entered STN:, (Jun. 24, 2008).
STN Columbus Registry, "RN: 831251-72-0," Entered STN:, (Feb. 15, 2005).
STN Columbus Registry. "RN: 476210-40-9," Entered STN:, (Dec. 13, 2002).
STN Columbus Registry. "RN: 940657-95-4," Entered STN:, (Jul. 2, 2007).
Parameshwer Makam, et al., European Journal of Medicinal Chemistry, 2014, 87, p. 643-656.
Sina Ghaemmaghami, et al., Journal of Virology, 2010, 84(7), p. 3408-3412.
Shirdhar Bhat, et al., Department of Pharmacology & Molecular Sciences, Johns Hopkins Bioorganic & Medicinal Chemistry Letters, 2013, 23(9), p. 2733-2737.
V. H. Patil, et al., Indian Journal of Chemistry, Section B: Organic Chemistry Including Medicinal Chemistry, 1979, 17B(5), p. 519-521.
Robert G. Gentles, et al., Bioorganic & Medicinal Chemistry Letters, 2008, 18(19), p. 5316-5319.
Registry (STN) [online], Aug. 22, 2008 [retrieved on Aug. 14, 2018], CAS registry No. 1042853-24-6, 1042868-31-4.
Registry (STN) [online], Jul. 31, 2009[retrieved on Aug. 14, 2018], CAS registry No. 1171310-23-8.
Registry (STN) [online], Jan. 2, 2002 [retrieved on Aug. 14, 2018], CAS registry No. 380174-17-4.
Registry (STN) [online], Mar. 6, 2003 [retrieved on Aug. 14, 2018], CAS registry No. 497083-40-6.
Registry (STN) [online], Mar. 19, 2001 [retrieved on Aug. 14, 2018], CAS registry No. 327971-37-9.
Registry (STN) [oniine], Aug. 28, 2011 [retrieved on Aug. 14, 2018], CAS registry No. 1324541-73-2.
Registry (STN) [online], Jan. 22, 2001 [retrieved on Aug. 14, 2018], CAS registry No. 315706-20-8.
Registry (STN) [online], Jun. 28, 2004 [retrieved on Aug. 14, 2018], CAS registry No. 700803-18-5.
Registry (STN) [online], Dec. 24, 2008 [retrieved on Aug. 14, 2018], CAS registry No. 1089559-86-3.
Registry (STN) [online], Jun. 24, 2008 [retrieved on Aug. 14, 2018], CAS registry No. 1030100-85-6.
Registry (STN) [online], Feb. 15, 2005 [retrieved on Aug. 14, 2018], CAS registry No. 831251-72-0.
English Translation of Notification of Reasons for Refusal from 2017-543900 dated Oct. 5, 2018.

* cited by examiner

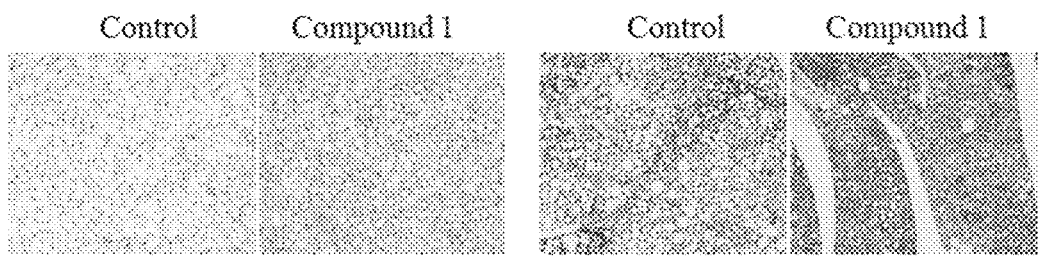

COMPOUNDS AND METHODS FOR INDUCING BROWNING OF WHITE ADIPOSE TISSUE

FIELD OF INVENTION

The present invention relates to a compound for inducing browning of white adipose tissue in vitro and in vivo, the preparation method thereof, as well as a composition comprising the same. Further, the present invention relates to the use of the compound and the method to treat metabolic disorders, such as obesity and diabetes.

BACKGROUND OF THE INVENTION

Adipose tissues can be traditionally classified into white adipose tissue (WAT) and brown adipose tissue (BAT). While WAT stores nutrients as lipids, BAT can dissipate lipids to provide heat in a process called thermogenesis. BAT thermogenesis is dependent on the activation of uncoupling protein-1 (UCP1), which is located in the inner mitochondrial membrane of BAT. When activated, UCP1 uncouples oxidative phosphorylation in mitochondria to dissipate the electrochemical gradient as heat.

In addition to the "classical" and "developmentally programmed" brown adipocytes clustered in defined anatomical BAT depots, a "browning" process, which consists of the induced appearance of UCP1-expressing and multilocular brown adipocytes in WAT depots, often in response to specific stimuli such as prolonged cold exposure and chronic treatment with β3-adrenergic stimuli. These inducible brown adipocytes within classical WAT depots have been called "brite" (brown-in-white) or "beige" adipocytes. The important roles of brite/beige cells in thermoregulation and energy homeostasis are highlighted recently. In adult humans, the predominant form of brown adipocytes is brite/beige cells, which can be induced from WAT under proper stimulation. In light of the promising metabolic benefits of brown adipocytes, intense research has been conducted in recent years to search for physiological, pharmacological and dietary agents that can enhance browning of WAT by induction of UCP1 expression or/and mitochondrial oxidative metabolism. So far, dozens of "browning" agents have been reported, including the sympathetic activators (such as the β3-adrenergic agonists BRL26830A and CL-316243), prostaglandins, PPARα and PPARγ agonists, retinoids, activators of AMP-activated protein kinase, thyroid hormone, bone morphogenetic protein 7 (BMP7), irisin and fibroblast growth factor (FGF)21. While most of these agents exert dual effects on both activation of classical BAT and induction of WAT browning, and some of them (such as prostaglandin, irisin and FGF21) are specific to the browning of WAT. Although some drugs are found to induce browning, they may show strong side effect. Therefore, it is important to look for safer and more effective "browning" food supplements and/or drugs for healthy development and treatment of obesity as well as it associated metabolic disorders.

SUMMARY OF THE INVENTION

The present invention generally provides a compound and a pharmaceutical composition thereof, wherein the compound is used to induce browning of white adipose tissue in vitro and in vivo, the preparation method thereof, as well as a composition comprising the same. Further, the present invention relates to the use of the compound and the method to treat metabolic disorders, such as obesity and diabetes.

In one aspect, the present invention provides a compound for inducing browning of white adipose tissue in vitro and in vivo, which has the structure of Formula I:

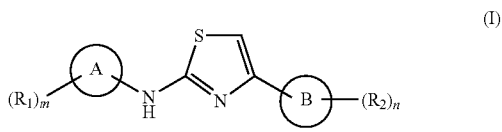

(I)

or a physiologically acceptable salt or hydrate or solvate thereof, wherein:
each of Ring A and Ring B are independently absent; or independently selected from the group consisting of phenyl, 3-7 membered saturated or partially unsaturated carbocyclic ring, 8-10 membered bicyclic saturated or partially unsaturated carbocyclic ring, 4-7 membered saturated or partially unsaturated heterocyclic ring having 1-2 heteroatoms independently selected from N, O and S, 5-6 membered monocyclic heteroaryl ring having 1-3 heteroatoms independently selected from N, O, and S, 7-10 membered bicyclic saturated or partially unsaturated heterocyclic ring having 1-4 heteroatoms independently selected from N, O and S, or 8-10 membered bicyclic heteroaryl ring having 1-4 heteroatoms independently selected from N, O and S;
each of $R_1$ and $R_2$ are independently selected from halogen, $C_1$-$C_6$ alkyl, $C_1$-$C_6$ haloalkyl, $C_2$-$C_6$ alkenyl, $C_2$-$C_6$ alkynyl, $C_1$-$C_6$ alkoxy, $C_1$-$C_6$ haloalkoxy, —$OR_3$, —$SR_3$, —$N(R_4)_2$, —CN, —$NO_2$, —$C(O)R_3$, —$C(S)R_3$, —$C(O)N(R_4)_2$, —$C(O)SR_3$, —$C(O)C(O)R_3$, —$C(O)CH_2C(O)R_3$, —$C(S)N(R_4)_2$, —$C(S)OR_3$, —$S(O)R_3$, —$SO_2N(R_4)_2$, —$N(R_4)C(O)R_3$, —$N(R_4)C(O)N(R_4)_2$, —$N(R_4)C(S)N(R_4)_2$, —$N(R_4)SO_2R_3$, —$N(R_4)SO_2N(R_4)_2$, —$N(R_4)N(R_4)_2$, —$N(R_4)C(=N(R_4))N(R_4)_2$, —$C=NN(R_4)_2$, —$C=NOR_3$, —$C(=N(R_4)_2$, —$OC(O)R_3$, or —$OC(O)N(R_4)_2$;
each of m and n are independently 0-4, as valency permits, and
each of $R_3$ and $R_4$ are independently hydrogen or an optionally substituted group selected from $C_1$-$C_6$ alkyl, $C_2$-$C_6$ alkenyl or $C_2$-$C_6$ alkynyl, each of which may be optionally substituted with halogen, amino, hydroxyl, alkoxy or cyano.

In a preferred embodiment of the present invention, there is provided a compound of the formula II

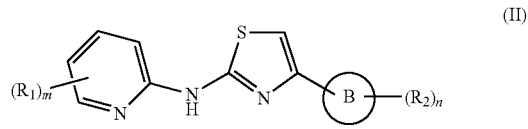

(II)

or pharmaceutically acceptable salt or hydrate or solvate thereof, wherein ring B, $R_1$, $R_2$, m and n are defined as in formula I.

In a preferred embodiment of the invention, there is provided a compound of the formula III

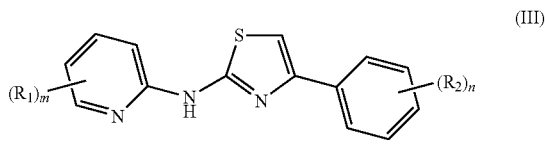

(III)

or pharmaceutically acceptable salt or hydrate or solvate thereof, wherein $R_1$, $R_2$, m and n are defined as in formula I.

In a preferred embodiment, example of the compound of the invention includes, but is not limited to 1. 4-(3,4-dimethoxyphenyl)-N-(pyridin-2-yl)thiazol-2-amine;
2. 4-(3,4-dimethoxyphenyl)-N-(4-methylpyridin-2-yl)thiazol-2-amine;
3. 4-(3-methoxyphenyl)-N-(pyridin-2-yl)thiazol-2-amine;
4. 4-phenyl-N-(pyridin-2-yl)thiazol-2-amine;
5. 5. 3-(2-(pyridin-2-ylamino)thiazol-4-yl)benzonitrile;
6. 6. 4-(3,4-dimethoxyphenyl)-N-(isoquinolin-3-yl)thiazol-2-amine;
7. 6. 4-(1H-indol-3-yl)-N-(pyridin-2-yl)thiazol-2-amine;
8. 4-(4-methoxyphenyl)-N-(pyridin-2-yl)thiazol-2-amine;
9. N-(pyridin-2-yl)-4-(pyridin-3-yl)thiazol-2-amine;
10. 4-(3,4-dimethoxyphenyl)-N-(6-methylpyridin-2-yl)thiazol-2-amine;
11. 4-(3,4-dimethoxyphenyl)-N-(5-methylpyridin-2-yl)thiazol-2-amine;
12. 4-(3,4-dimethoxyphenyl)-N-(3-methylpyridin-2-yl)thiazol-2-amine;
13. N-(4-chloropyridin-2-yl)-4-(3,4-dimethoxyphenyl)thiazol-2-amine;
14. N-(4-(3,4-dimethoxyphenyl)thiazol-2-yl)-6-methylbenzo[d]thiazol-2-amine;
15. 4-(2,4-dimethoxyphenyl)-N-(pyridin-2-yl)thiazol-2-amine;
16. 4-(4-(dimethylamino)phenyl)-N-(pyridin-2-yl)thiazol-2-amine;
17. N-(pyridin-2-yl)-4-(3,4,5-trimethoxyphenyl)thiazol-2-amine;
18. 4-(3,5-dimethoxyphenyl)-N-(pyridin-2-yl)thiazol-2-amine;
19. 4-(3,4-dimethoxyphenyl)-5-methyl-N-(pyridin-2-yl)thiazol-2-amine;
20. 4-(3,4-dimethoxyphenyl)-N-phenylthiazol-2-amine;
21. N-(pyridin-2-yl)-4-p-tolylthiazol-2-amine;
22. 4-(4-fluorophenyl)-N-(pyridin-2-yl)thiazol-2-amine;
23. N-(pyridin-2-yl)-4-(4-(trifluoromethoxy)phenyl)thiazol-2-amine;
24. 4-(2-methoxyphenyl)-N-(pyridin-2-yl)thiazol-2-amine;
25. 4-(4-bromo-2-methoxyphenyl)-N-(pyridin-2-yl)thiazol-2-amine;
26. N-(pyridin-2-yl)-4-(pyridin-4-yl)thiazol-2-amine;
27. N,4-di(pyridin-2-yl)thiazol-2-amine;
28. 4-(2-bromo-4-morpholinophenyl)-N-(pyridin-2-yl)thiazol-2-amine;
29. N-(4-(3,4-dimethoxyphenyl)thiazol-2-yl)acetamide;
30. N-(4-(3,4-dimethoxyphenyl)thiazol-2-yl)benzamide;
31. 4-(3,4-dimethoxyphenyl)-N-methylthiazol-2-amine;
32. N-(4-(3,4-dimethoxyphenyl)thiazol-2-yl)picolinamide;
33. 4-(3,4-dimethoxyphenyl)-N-(pyridin-3-yl)thiazol-2-amine;
34. 4-(4-nitrophenyl)-N-(pyridin-2-yl)thiazol-2-amine;
35. 4-(4-aminophenyl)-N-(pyridin-2-yl)thiazol-2-amine;
36. N-(4-(2-(pyridin-2-ylamino)thiazol-4-yl)phenyl)acetamide;
37. 1-isopropyl-3-(4-(2-(pyridin-2-ylamino)thiazol-4-yl)phenyl)urea;
38. N-(4-(2-(pyridin-2-ylamino)thiazol-4-yl)phenyl)propionamide;
39. N-(4-(2-(pyridin-2-ylamino)thiazol-4-yl)phenyl)butyramide;
40. 4-(4-bromophenyl)-N-(pyridin-2-yl)thiazol-2-amine;
41. 4-(2-(pyridin-2-ylamino)thiazol-4-yl)phenol;
42. 4-(4-isopropoxyphenyl)-N-(pyridin-2-yl)thiazol-2-amine;
43. 4-(4-butoxyphenyl)-N-(pyridin-2-yl)thiazol-2-amine;
44. ethyl 2-(4-(2-(pyridin-2-ylamino)thiazol-4-yl)phenoxy)acetate;
45. 2-(4-(2-(pyridin-2-ylamino)thiazol-4-yl)phenoxy)acetic acid;
46. 1-morpholino-2-(4-(2-(pyridin-2-ylamino)thiazol-4-yl)phenoxy)ethanone;
47. N-ethyl-2-(4-(2-(pyridin-2-ylamino)thiazol-4-yl)phenoxy)acetamide;
48. methyl 4-(2-(pyridin-2-ylamino)thiazol-4-yl)benzoate;
49. 4-(2-(pyridin-2-ylamino)thiazol-4-yl)benzonitrile;
50. 4-(biphenyl-4-yl)-N-(pyridin-2-yl)thiazol-2-amine;
51. 4-(4-(methylsulfonyl)phenyl)-N-(pyridin-2-yl)thiazol-2-amine;
52. morpholino(4-(2-(pyridin-2-ylamino)thiazol-4-yl)phenyl)methanone;
53. N-ethyl-4-(2-(pyridin-2-ylamino)thiazol-4-yl)benzamide;
54. 4-(4-(morpholinomethyl)phenyl)-N-(pyridin-2-yl)thiazol-2-amine;
55. 4-(4-(benzylamino)phenyl)-N-(pyridin-2-yl)thiazol-2-amine;
56. 4-(4-(neopentylamino)phenyl)-N-(pyridin-2-yl)thiazol-2-amine;
57. N-isopropyl-4-(2-(pyridin-2-ylamino)thiazol-4-yl)benzamide;
58. N-phenyl-4-(2-(pyridin-2-ylamino)thiazol-4-yl)benzamide;
59. (4-methylpiperazin-1-yl)(4-(2-(pyridin-2-ylamino)thiazol-4-yl)phenyl)methanone;
60. 4-(2-(pyridin-2-ylamino)thiazol-4-yl)benzyl acetate;
61. 1-(4-(4-(2-(pyridin-2-ylamino)thiazol-4-yl)phenyl)piperidin-1-yl)ethanone;
62. N-(2-(2-methoxyethoxy)ethyl)-4-(2-(pyridin-2-ylamino)thiazol-4-yl)benzamide;
63. 4-(4-chlorophenyl)-N-(pyridin-2-yl)thiazol-2-amine;
64. 4-(2-(pyridin-2-ylamino)thiazol-4-yl)-N-(pyridin-3-yl)benzamide;
65. 4-(2-(pyridin-2-ylamino)thiazol-4-yl)-N-(pyridin-4-yl)benzamide;
66. N,N-diethyl-4-(2-(pyridin-2-ylamino)thiazol-4-yl)benzamide;
67. (S)-ethyl 1-(4-(2-(pyridin-2-ylamino)thiazol-4-yl)benzoyl)pyrrolidine-2-carboxylate;
68. N-(4-chlorophenyl)-2-(pyridin-2-ylamino)thiazole-4-carboxamide
69. N-(pyridin-2-yl)-4-(2-(pyridin-2-ylamino)thiazol-4-yl)benzamide;
70. (S)—N-(4-(3,4-dimethoxyphenyl)thiazol-2-yl)pyrrolidine-2-carboxamide;
71. (S)-ethyl 2-(4-(3,4-dimethoxyphenyl)thiazol-2-ylcarbamoyl)pyrrolidine-1-carboxylate;
72. 4-(4-(piperidin-1-ylmethyl)phenyl)-N-(pyridin-2-yl)thiazol-2-amine;
73. 1-(4-(2-(pyridin-2-ylamino)thiazol-4-yl)phenyl)ethanone;
74. N-hydroxy-4-(2-(pyridin-2-ylamino)thiazol-4-yl)benzamide;
75. 4-(2,3-dichlorophenyl)-N-(pyridin-2-yl)thiazol-2-amine;
76. N-(pyridin-2-yl)-4-(4-(thiophen-3-yl)phenyl)thiazol-2-amine;
77. 4-(4-(2H-tetrazol-5-yl)phenyl)-N-(pyridin-2-yl)thiazol-2-amine;
78. 4-(4-ethynylphenyl)-N-(pyridin-2-yl)thiazol-2-amine;

79. N-(pyridin-2-yl)-4-(4-(pyridin-4-yl)phenyl)thiazol-2-amine;
80. 4-(3,4-dimethylphenyl)-N-(pyridin-2-yl)thiazol-2-amine;
81. 4-(2,3-dihydro-1H-inden-5-yl)-N-(pyridin-2-yl)thiazol-2-amine;
82. 4-(benzo[d][1,3]dioxol-5-yl)-N-(pyridin-2-yl)thiazol-2-amine;
83. 4-(4-amino-3-methylphenyl)-N-(pyridin-2-yl)thiazol-2-amine.

In another aspect, the present invention provides a pharmaceutical composition comprising the compound or physiologically acceptable salt or hydrate or solvate thereof of the present invention and at least one pharmaceutically acceptable carrier or diluent, wherein said compound is in free form or in a pharmaceutically acceptable salt form. Such composition may be an oral composition, injectable composition or suppository. And the composition may be manufactured in a conventional manner by mixing, granulating or coating methods.

In an embodiment of the invention, the composition is an oral composition and it may be a tablet or gelatin capsule. Preferably, the oral composition comprises the present compound together with a) diluents, e.g., lactose, dextrose, sucrose, mannitol, sorbitol, cellulose and/or glycine; b) lubricants, e.g., silica, talcum, stearic acid, its magnesium or calcium salt and/or polyethyleneglycol; for tablets, together with c) binders, e.g., magnesium aluminum silicate, starch paste, gelatin, tragamayth, methylcellulose, sodium carboxymethylcellulose and or polyvinylpyrrolidone; and if desired, d) disintegrants, e.g., starches, agar, alginic acid or its sodium salt, or effervescent mixtures; and/or e) additives, e.g., absorbents, colorants, flavors and sweeteners.

In another embodiment of the invention, the composition is an injectable composition, and may be an aqueous isotonic solution or suspension.

In yet another embodiment of the invention, the composition is a suppository and may be prepared from fatty emulsion or suspension.

Preferably, the composition is sterilized and/or contains adjuvant. Such adjuvant can be preserving, stabilizing, wetting or emulsifying agent, solution promoter, salt for regulating the osmotic pressure, buffer and/or any combination thereof.

Alternatively or in addition, the composition may further contain other therapeutically valuable substances for different applications, like solubilizers, stabilizers, tonicity enhancing agents, buffers and/or preservatives.

In an embodiment of the invention, the composition may be a formulation suitable for transdermal application. Such formulation includes an effective amount of the compound of the present invention and a carrier. Preferably, the carrier may include absorbable pharmacologically acceptable solvents to assist passage through the skin of the host. A transdermal device contain the formulation may also be used. The transdermal device may be in the form of a bandage comprising a backing member, a reservoir containing the compound optionally with carriers, optionally a rate controlling barrier to deliver the compound to the skin of the host at a controlled and predetermined rate over a prolonged period of time, and means to secure the device to the skin. Otherwise, a matrix transdermal formulation may also be used.

In another embodiment of the invention, the composition may be a formulation suitable for topical application, such as to the skin and eyes, and may be aqueous solution, ointment, cream or gel well known in the art.

In another aspect, the present invention provides a method of inhibiting WAT secretion from a cell by using the compound or composition of the present invention.

For therapeutical use, the compound of the present invention could be administered in a therapeutically effective amount via any acceptable way known in the art singly. As used herein, the therapeutically effective amount may vary widely depending on the severity of the disease, the age and relative health of the subject, the potency of the compound used and other factors. Generally, the satisfactory result is indicated to be obtained systemically at a daily dosage of about 0.03 to 2.5 mg/kg per body weight of the subject. In one embodiment, the indicated daily dosage for larger mammal as human is in the range from about 0.5 mg to about 100 mg. Preferably, the compound is administered in divided doses up to four times a day or in retard form. In another embodiment, suitable unit dosage forms for oral administration comprise from 1 to 100 mg active ingredient.

Alternatively, the compound of the present invention may be administered in a therapeutically effective amount as the active ingredient in combination with one or more therapeutic agents, such as pharmaceutical combinations. There may be synergistic effects when the compound of the present invention is used with a chemotherapeutic agent known in the art. The dosage of the co-administered compounds could vary depending on the type of co-drug employed, the specific drug employed, the condition being treated and so forth.

The compound of the present invention or the composition thereof may be administered by any conventional route. In one embodiment, it is administered enterally, such as orally, and in the form of tablets or capsules. In another embodiment, it is administered parenterally and in the form of injectable solutions or suspensions. In yet another embodiment, it is administered topically and in the form of lotions, gels, ointments or creams, or in a nasal or suppository form.

In another aspect, the invention also provides a pharmaceutical combination, preferably, a kit, comprising a) a first agent which is the compound of the present invention as disclosed herein, in free form or in pharmaceutically acceptable salt form, and b) at least one co-agent. In addition, the kit may comprise instructions for its administration.

The combination of the present invention may be used in vitro or in vivo. Preferably, the desired therapeutic benefit of the administration may be achieved by contacting cell, tissue or organism with a single composition or pharmacological formulation that includes the compound of the present invention and one or more agents, or by contacting the cell, tissue or organism with two or more distinct compositions or formulations, wherein one composition includes one agent and the other includes another. The agents of the combination may be administered at the same time or separately within a period of time. Preferably, the separate administration can result in a desired therapeutic benefit. The present compound may precede, be co-current with and/or follow the other agents by intervals ranging from minutes to weeks. A person skilled in the art could generally ensure the interval of the time of each delivery, wherein the agents administered separately could still be able to exert an advantageously combined effect on the cell, tissue or organism. In one embodiment, it is contemplated that one may contact the cell, tissue or organism with two, three, four or more modalities substantially simultaneously as the candidate substance, i.e., with less than about one minute. In another embodiment, one or more agents may be administered about between 1 minute to 14 days.

In another aspect, the present provides a process for preparing the compound of the present invention or the salts or derivatives thereof.

In one embodiment, the compound having Formula (I) may be prepared following any one of the synthetic methodologies described in embodiments below. In the reactions described, reactive functional groups, for example hydroxy, amino, imino, thio or carboxy groups, where these are desired in the final product, may be protected to avoid their unwanted participation in the reactions. Conventional protecting groups may be used in accordance with standard practice (see e.g., T. W. Greene and P. G. M. Wuts in "Protective Groups in Organic Chemistry", John Wiley and Sons, 1991). Suitable leaving groups for use in the synthetic methodologies described include halogen leaving groups and other conventional leaving groups known in the art. Preferably, the leaving group is chloro or bromo.

In another embodiment, the compound of the invention or the salts thereof may also be obtainable in the form of hydrates, or their crystals which may include for example the solvent used for crystallization (present as solvates). Salts can usually be converted to compounds in free form by treating with suitable basic agents, preferably with alkali metal carbonates, alkali metal hydrogen carbonates, or alkali metal hydroxides, more preferably with potassium carbonate or sodium hydroxide. A compound of the invention in a base addition salt form may be converted to the corresponding free acid by treating with a suitable acid, such as hydrochloric acid. In view of the close relationship between the novel compounds in free form and those in the form of their salts, including those salts that may be used as intermediates, for example in the purification or identification of the novel compounds, any reference to the free compounds is to be understood as referring also to the corresponding salts, as appropriate.

Salts of the present compound with a salt-forming group may be prepared in a manner known in the art. Acid addition salts of compound of Formula (I) may thus be obtained by treatment with an acid or with a suitable anion exchange reagent.

Pharmaceutically acceptable salts of the compound of the invention may be formed as acid addition salts from compound of Formula (I) with a basic nitrogen atom with organic or inorganic acids.

Preferably, suitable inorganic acids include, but are not limited to, halogen acids, such as hydrochloric acid, sulfuric acid, or phosphoric acid.

Preferably, suitable organic acids include, but are not limited to, carboxylic, phosphoric, sulfonic or sulfamic acids, for example acetic acid, propionic acid, octanoic acid, decanoic acid, dodecanoic acid, glycolic acid, lactic acid, fumaric acid, succinic acid, adipic acid, pimelic acid, suberic acid, azelaic acid, -malic acid, tartaric acid, citric acid, amino acids, such as glutamic acid or aspartic acid, maleic acid, hydroxymaleic acid, methylmaleic acid, cyclohexanecarboxylic acid, adamantanecarboxylic acid, benzoic acid, salicylic acid, 4 aminosalicylic acid, phthalic acid, phenylacetic acid, mandelic acid, cinnamic acid, methane- or ethane-sulfonic acid, 2-hydroxyethanesulfonic acid, ethane-1,2-disulfonic acid, benzenesulfonic acid, 2-naphthalenesulfonic acid, 1,5-naphthalene-disulfonic acid, 2-, 3- or 4 methylbenzenesulfonic acid, methylsulfuric acid, ethylsulfuric acid, dodecylsulfuric acid, N cyclohexylsulfamic acid, N-methyl-, N-ethyl- or N-propyl-sulfamic acid, or other organic protonic acids, such as ascorbic acid.

Alternatively, it is also possible to use pharmaceutically unacceptable salts for isolation or purification, for example picrates or perchlorates. But for therapeutic use, only pharmaceutically acceptable salts or free compounds are employed, where applicable in the form of pharmaceutical preparations.

In yet another embodiment, compound of the present invention in unoxidized form may be prepared from N-oxides of compound of the invention by treating with a reducing agent in a suitable inert organic solvent at 0 to 80° C. Preferably, the reducing agent is sulfur, sulfur dioxide, triphenyl phosphine, lithium borohydride, sodium borohydride, phosphorus trichloride, tribromide, or the like. Preferably, the invert organic solvent is acetonitrile, ethanol, aqueous dioxane, or the like.

In yet another embodiment, prodrug derivatives of the compound of the present invention may be prepared by methods known in the art (for further details see Saulnier et al., (1994), Bioorganic and Medicinal Chemistry Letters, Vol. 4, p. 1985). In a preferable embodiment, an appropriate prodrug may be prepared by reacting a non-derivatized compound of the invention with a suitable carbamylating agent such as 1,1-acyloxyalkylcarbanochloridate, para-nitrophenyl carbonate, or the like.

In yet another embodiment, protected derivatives of the compound of the present invention may be made by means known in the art. A detailed description of techniques applicable to the creation of protecting groups and their removal may be found in T. W. Greene, "Protecting Groups in Organic Chemistry", 3rd edition, John Wiley and Sons, Inc., 1999.

In yet another embodiment, the present invention also includes isotopically-labeled compounds of the present invention, wherein one or more atoms are replaced by one or more atoms having specific atomic mass or mass numbers. Examples of isotopes that can be incorporated into compounds of the invention include, but are not limited to, isotopes of hydrogen, carbon, nitrogen, oxygen, fluorine, sulfur, and chlorine (such as $^2H$, $^3H$, $^{11}C$, $^{13}C$, $^{14}C$, $^{15}N$, $^{17}O$, $^{18}O$, $^{35}S$, $^{18}F$, $^{36}Cl$). Isotopically-labeled compounds of the present invention are useful in assays of the tissue distribution of the compounds and their prodrugs and metabolites; preferred isotopes for such assays include $^3H$ and $^{14}C$. In addition, in certain circumstances substitution with heavier isotopes, such as deuterium ($^2H$ or D), can provide increased metabolic stability, which offers therapeutic advantages such as increased in vivo half-life or reduced dosage requirements. Isotopically-labeled compounds of this invention can generally be prepared according to the methods described herein by substituting an isotopically-labeled reagent for a non-isotopically labeled reagent.

In yet another embodiment, compound of the present invention may be prepared as their individual stereoisomers. The process includes reacting a racemic mixture of the compound with an optically active resolving agent to form a pair of diastereoisomeric compounds, separating the diastereomers and recovering the optically pure enantiomers. Resolution of enantiomers may be carried out using covalent diastereomeric derivatives of the compound of the present invention, or by using dissociable complexes such as crystalline diastereomeric salts. Diastereomers have distinct physical properties presented by melting points, boiling points, solubilities, reactivity, etc., and may be readily separated by taking advantage of these dissimilarities. The diastereomers may be separated by fractionated crystallization, chromatography, or by separation/resolution techniques based upon differences in solubility. The optically pure enantiomer is then recovered, along with the resolving agent, by any practical means that would not result in racemization. A more detailed description of the techniques applicable to the resolution of stereoisomers of compounds from their racemic mixture may be found in Jean Jacques, Andre Collet, Samuel H. Wilen, "Enantiomers, Racemates and Resolutions", John Wiley And Sons, Inc., 1981.

In conclusion, the compound of the present invention could be made by the process described below; optionally a pharmaceutically acceptable salt may be converted from the compound of the present invention; optionally a pharmaceutically acceptable N-oxide may be converted from an unoxidized form of the compound the present invention; optionally an individual isomer of the compound of the present invention is resolved from a mixture of isomers; and optionally a pharmaceutically acceptable prodrug derivative may be converted from a non-derivatized compound of the present invention.

Insofar as the production of the starting materials is not particularly described, the compounds are known or can be prepared analogously to methods known in the art or as disclosed in the examples hereinafter. One of skill in the art will appreciate that the above transformations are only representative of methods for preparation of the compounds of the present invention, and that other well-known methods can similarly be used.

In another aspect, the present invention also provides the use of the compounds of formula I or the composition thereof in the preparation of medicines for treating metabolic disorders, such as obesity and diabetes.

In another aspect, the present invention also provides a method for inducing browning of white adipose tissue in vitro and in vivo by using the compounds or the composition of the present invention.

In another aspect, the present invention also provides a method for treating metabolic disorders, such as obesity and diabetes, by administering a therapeutically effective amount of the compounds or the composition of the present invention.

DESCRIPTION OF THE FIGURES

FIG. 1: Compound 1 promotes browning of adipose tissue from 16-week-old obese mice induced by high fat diets for 8-week. Hematoxylin and eosin staining (left panel) and UCP1 immunochemistry (right panel) analysis of adipose tissue in mice treated with compound 1 compared with control group, showing browning effects of white adipose tissue in the embodiment of reduced cell size and increased cell number.

EMBODIMENTS

Abbreviation Definition or Explanation
DCE 1,2-Dichloroethane
DCM Dichloromethane
DIPEA N,N'-Diisopropylethylamine
DMF N,N-Dimethylformamide
eq. equivalents
EDCI 1-ethyl-3-(3-dimethylaminopropyl)carbodiimide hydrochlide
HOBt N-hydroxybenzotriazole
NBS N-bromosuccinimide
TEA triethylamine
THF tetrahydrofuran
Methods of Preparation The compounds of the present invention may be prepared by methods as those illustrated in the following scheme I to II. Starting materials are commercially available or prepared by the methods as those illustrated in the following scheme III to V. Additional methods for making selected compounds of the present invention are provided below. Solvents, temperatures, pressures and other reaction conditions may readily be selected by one of ordinary skill in the art.

Scheme I

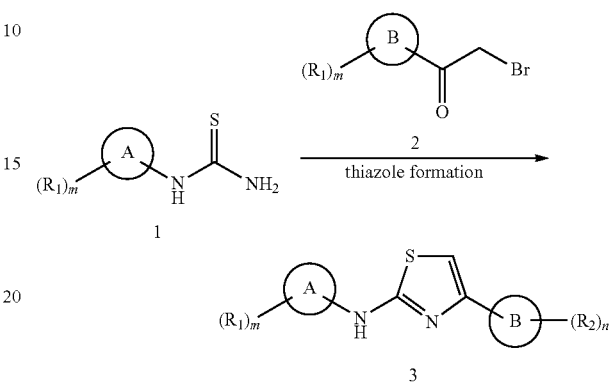

General Protocol for the Thiazole Compound 3 Formation

To a solution of substituted thiourea 1 (1.0 eq.) in alcoholic solvent (about 0.5 M concentration) such as, but not limited to, methanol, ethanol or isopropanol was added substituted α-bromoketone 2 (1.0 eq.), and the mixture was heated to reflux for 3~8 h until the starting material was consumed. The mixture was then cooled to room temperature, evaporated under reduced pressure and purified by silica gel chromatography to give compound 3 of the present invention in 60~95% yield, such as the compounds 1-28, 31 and 33-83 listed below.

Scheme II

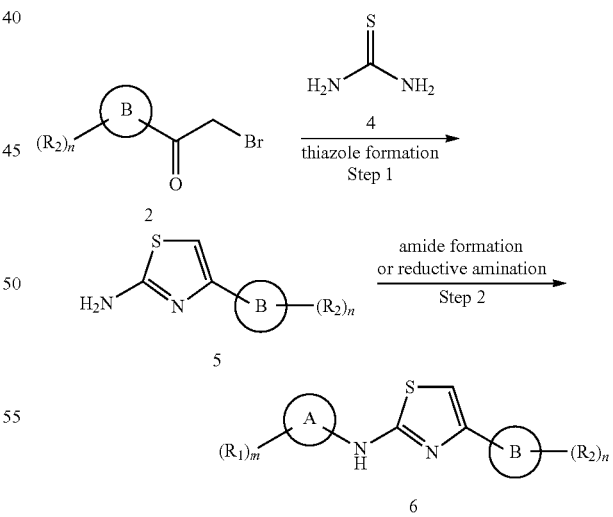

Step 1 General Protocol for the 2-aminothiazole 5 Formation

To a solution of thiourea 4 (1.0 eq.) in alcoholic solvent (about 0.5 M concentration) such as, but not limited to, methanol, ethanol or isopropanol was added α-bromoketone 2 (1.0 eq.), and the mixture was heated to reflux for 3~8 h until the starting material was consumed. Then the mixture was cooled to room temperature, evaporated under reduced pressure and purified by silica gel chromatography to give 2-aminothiazole 5 of scheme II in 60~95% yield.

Step 2 General Protocol for the Thiazole Compound 6 Formation 2-aminothiazole 5 (1.0 eq.) obtained from step 1 of scheme II was reacted with substituted acyl chloride (1.5 eq.) in the presence of a base (2.2 eq.) such as, but not limited to TEA, DIPEA, $Na_2CO_3$ in organic solvent (about 0.5 M concentration) such as, but not limited to DCM, DMF or $CH_3CN$ to form amide compound 6 of the present invention in 60~95% yield, such as the compounds 29 and 30 listed below.

or 2-aminothiazole 5 (1.0 eq.) obtained from step 1 of scheme II was coupled with substituted carboxylic acid (1.1 eq.) in the presence of classical coupling reagents (1.1 eq.) in amide synthesis such as, but not limited to, EDCl/HOBt/DIPEA combination in organic solvents (about 0.5 M concentration) such as, but not limited to, DCM, THF or DMF to afford amide compound 6 of present invention in 55~85% yield, such as the compounds 32 listed below.

General Procedure for the Preparation of Thiourea Intermediates 1 from Amines

The substituted thiourea intermediates 1 of scheme I were commercially available or prepared according to procedures provided in the following scheme III.

Scheme III

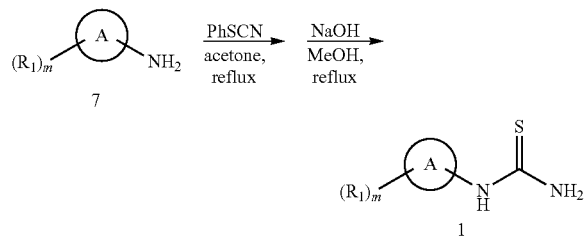

Phenyl isothiocyanate (1.1 eq.) was added dropwise to a stirred solution of amine 7 (1.0 eq.) in organic solvent (about 0.1 M concentration) such as, but not limited to, acetone, THF or $CH_3CN$ at room temperature. The reaction mixture was heated to reflux for 1-3 h until the amine 7 was consumed. Then the mixture was cooled to room temperature, poured into water-ice, and stirred for an additional 15 min. The benzoyl thiourea precipitate was collected by filtration and washed with more water. This crude material was dissolved in methanol (about 0.05M concentration) and treated with aqueous 1N NaOH (2 eq.) and heated to 80° C. until the hydrolysis was completed. After cooling, the mixture was poured into water-ice and sufficient aqueous 1N HCl was added to produce a neutral (pH about 7) solution. The thiourea intermediate typically precipitates from the neutral solution and was collected by filtration and dried. This two-step procedure provides thiourea intermediates in 50~95% overall yield. The thiourea intermediates can be used directly in the next step without further purification.

General Procedure for the Preparation of Substituted α-bromoketone Intermediates 2

The substituted α-bromoketone intermediates 2 of schemes I to II were commercially available or prepared according to procedures provided in the following scheme IV to V.

Scheme IV

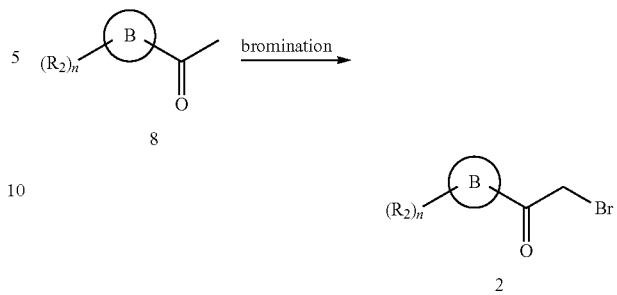

To a solution of ketone 8 (1.0 eq.) in organic solvent (about 0.5M concentration) such as, but not limited to, DCM, chloroform or ether was added bromine (1.0 eq.) dropwise at 0° C. The mixture was then warmed to room temperature or elevated temperature (50~90° C.) if necessary and stirred for 2~6 h until the ketone was consumed. The mixture was then extracted, dried, evaporated and purified by silica gel chromatography to give compound 2 of scheme IV in 70~95% yield.

When ketones were commercially unavailable, α-bromoketone intermediates 2 were prepared in an alternative way provided in the following scheme V.

Scheme V

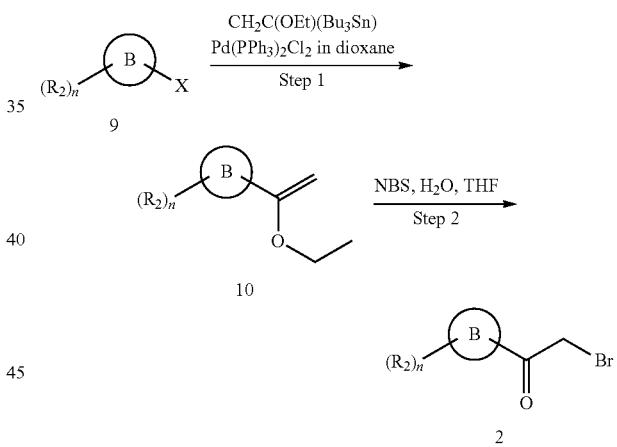

Step 1 General Procedure for the Preparation of Ethoxyethene Intermediates 10 Via Stile Coupling Reaction To a solution of halogenated compound 9 (1.0 eq.) in organic solvent (about 1M concentration) such as, but not limited to, dioxane, DCE or toluene was added tributyl (1-ethoxyvinyl)tin (1.5 eq.) and dichlorobis(triphenylphosphine)palladium (II) (0.05 eq.). The mixture was purged with nitrogen for 5 min, and stirred at elevated temperature (90~120° C.) in a sealed tube for 12~18 h until the compound 9 was consumed. The mixture was then cooled to room temperature, extracted, dried, evaporated and purified by silica gel chromatography to give compound 10 of scheme V in 65~85% yield.

Step 2 General Procedure for the Preparation of α-bromoketone Intermediates 2 Via Bromination of Intermediates 10

To a solution of compound 10 (1.0 eq.) in THF/$H_2O$ (about 0.5M concentration, $V_{THF}:V_{H2O}=3:1$) was added NBS (1.0 eq.). The mixture was stirred at room temperature for 10~30 min, then extracted, dried, evaporated and purified by silica gel chromatography to afford α-bromoketone intermediates 2 of scheme V in 55~75% yield.

Detailed Embodiments

The present invention is further exemplified, but not limited, by the following and examples that illustrate the preparation of the compounds of the invention.

The invention will now be further described by the following working examples, which are preferred embodiments of the invention. All temperatures are in degrees Celsius (° C.) unless otherwise indicated. Preparative Reverse Phase (RP) HPLC purifications were done on C18 reverse phase (RP) columns using water/methanol mixtures. All the synthesized compounds were characterized by at least NMR or LC/MS. During work up of reactions, the organic extract was dried over sodium sulfate, purified by silica gel column chromatography or (RP) HPLC, unless mentioned otherwise.

These examples are illustrative rather than limiting and it is to be understood that there may be other embodiments that fall within the spirit and scope of the invention as defined by the claims appended hereto.

EXAMPLE 1

The Preparation of Compound 1

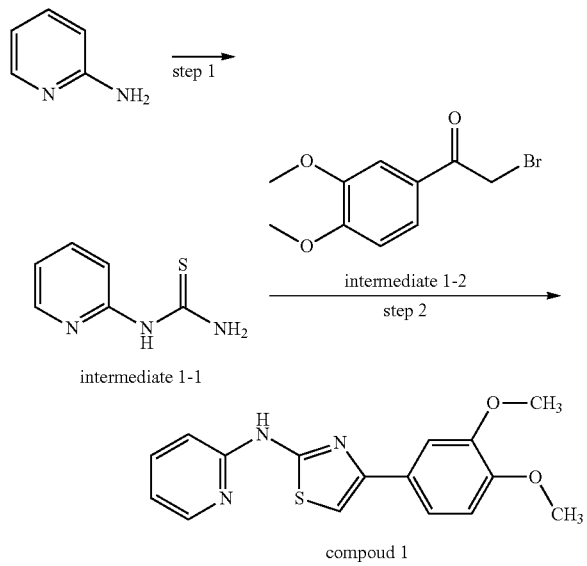

Step 1 Preparation of Intermediate 1-1

Phenyl isothiocyanate (13.52 g, 0.1 mol) was added dropwise to a stirred solution of 2-aminopyridine (9.41 g, 0.1 mol) in 200 mL acetone at room temperature. The reaction mixture was heated to reflux for 3 h until the 2-aminopyridine was consumed. Then the mixture was cooled to room temperature, poured into water-ice, and stirred for an additional 15 min. The benzoyl thiourea precipitate was collected by filtration and washed with more water. This crude material was dissolved in 200 mL methanol and treated with 200 mL aqueous 1N NaOH and heated to 80° C. until the hydrolysis was completed. After cooling, the mixture was poured into water-ice and sufficient aqueous 1N HCl was added to produce a neutral (pH about 7) solution. The thiourea intermediate precipitate was collected by filtration and dried, providing 13.9 g of intermediate 1-1 in 91% yield. ESI-MS m/z 154.0 [M+H].

Step 2 Preparation of Compound 1

To a solution of intermediate 1-1 (0.153 g, 1.0 mmol) in 5 mL ethanol was added 2-bromo-1-(3,4-dimethoxyphenyl)ethanone 2 (0.259 g, 1.0 mmol), and the mixture was heated to reflux for 3 h until the starting material was consumed. The mixture was then cooled to room temperature, evaporated under reduced pressure and purified by silica gel chromatography to give 0.266 g of compound 1 of the present invention in 85% yield. ¹H NMR (400 MHz, CDCl3) δ 9.84 (s, 1H), 8.34 (dd, J=5.0, 1.0 Hz, 1H), 7.49-7.39 (m, 3H), 6.94 (s, 1H), 6.90-6.86 (m, 1H), 6.86-6.80 (m, 1H), 6.58 (d, J=8.3 Hz, 1H), 3.92 (s, 3H), 3.86 (s, 3H). ESI-MS m/z 314.3 [M+H].

EXAMPLE 2

The Preparation of Compound 18

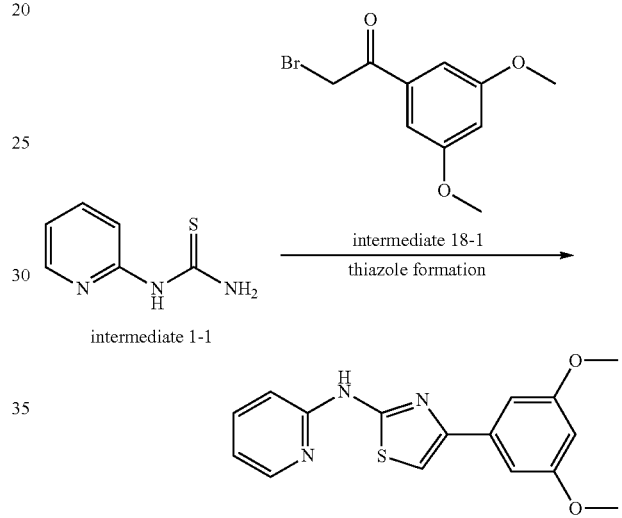

To a solution of intermediate 1-1 (0.153 g, 1.0 mmol) in 5 mL ethanol was added 2-bromo-1-(3,5-dimethoxyphenyl)ethanone intermediate 18-1 (0.259 g, 1.0 mmol), and the mixture was heated to reflux for 3 h until the starting material was consumed. The mixture was then cooled to room temperature, evaporated under reduced pressure and purified by silica gel chromatography to give 0.261 g of compound 18 of the present invention in 84% yield. ¹H NMR (400 MHz, CDCl₃) δ 9.88 (s, 1H), 8.46-8.09 (m, 1H), 7.47-7.32 (m, 3H), 7.16 (s, 1H), 6.98 (d, J=2.4 Hz, 2H), 6.49 (d, J=2.4 Hz, 1H), 3.94 (s, 3H), 3.82 (s, 3H). ESI-MS m/z 314.3 [M+H].

EXAMPLE 3

The Preparation of Compound 32

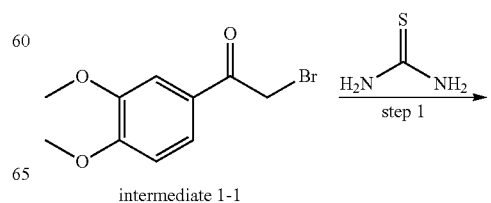

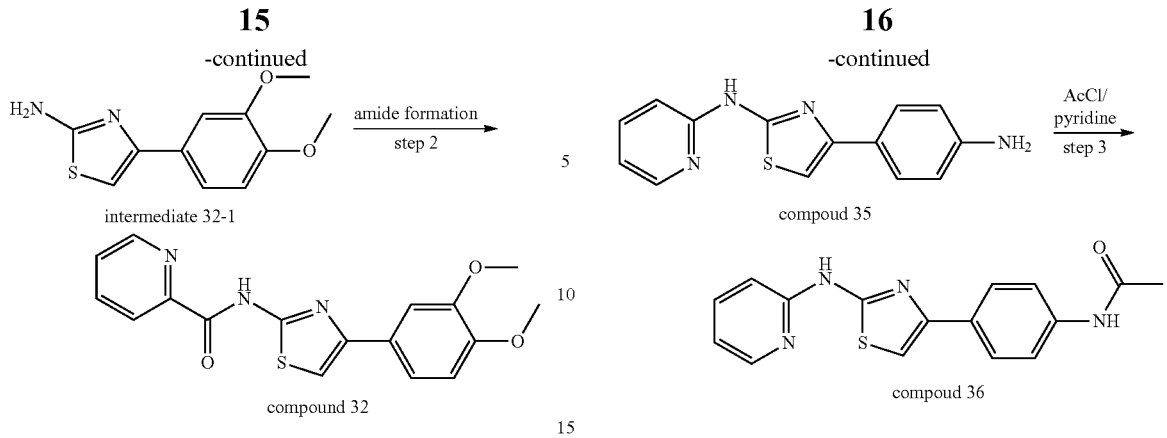

intermediate 32-1 compound 32 compound 35 compound 36

Step 1 Preparation of intermediate 32-1 To a solution of thiourea (7.61 g, 0.1 mol) in 200 mL ethanol was added intermediate 1-1 (25.9 g, 0.1 mol), and the mixture was heated to reflux for 3~8 h until the starting material was consumed. Then the mixture was cooled to room temperature, evaporated under reduced pressure and purified by silica gel chromatography to give 18.9 g of intermediate 32-1 in 85% yield. $^1$H NMR (400 MHz, CDCl$_3$) δ 7.38-7.27 (m, 2H), 6.88 (d, J=8.2 Hz, 1H), 6.60 (s, 1H), 5.04 (s, 2H), 3.95 (s, 3H), 3.90 (s, 3H). ESI-MS m/z 237.3 [M+H].

Step 2 Preparation of Compound 32

To a solution of 2-picolinic acid (21.17 mg, 0.172 mmol) in 5 mL DCM were added EDCI (36.1 mg, 0.189 mmol), HOBt (25.5 mg, 0.189 mmol), DIPEA (48.9 mg, 0.378 mmol) and the mixture was stirred at room temperature for 15 min. Then intermediate 32-1 (40.6 mg, 0.172 mmol) was added. The mixture was continued to stir at room temperature for 12 h until intermediate 32-1 was consumed, then evaporated, under reduced pressure and the crude material was purified by silica gel chromatography to give 45.8 mg of compound 32 in 78% yield. $^1$H NMR (400 MHz, CDCl$_3$) δ 11.23 (s, 1H), 8.69 (d, J=4.8 Hz, 1H), 8.31 (d, J=7.8 Hz, 1H), 7.96 (t, J=7.0 Hz, 1H), 7.55 (dd, J=7.4, 5.0 Hz, 1H), 7.47 (s, 1H), 7.46-7.41 (m, 1H), 7.11 (s, 1H), 6.93 (d, J=8.3 Hz, 1H), 3.99 (s, 3H), 3.93 (s, 3H). ESI-MS m/z 342.3 [M+14].

EXAMPLE 4

The Preparation of Compound 36

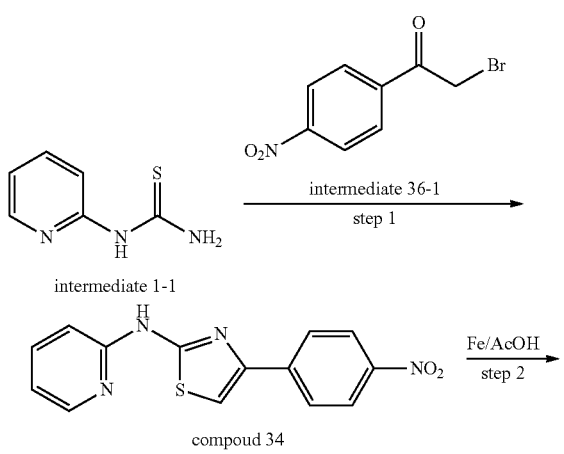

Step 1 Preparation of Compound 34

To a solution of intermediate 1-1 (15.3 g, 0.1 mol) in 200 mL ethanol was added intermediate 36-1 (24.4 g, 0.1 mol), and the mixture was heated to reflux for 3 h until the starting material was consumed. The mixture was then cooled to room temperature, evaporated under reduced pressure and purified by silica gel chromatography to give 27.98 g of compound 34 of the present invention in 94% yield. $^1$H NMR (400 MHz, DMSO) δ 11.53 (s, 1H), 8.30 (dd, J=12.9, 6.7 Hz, 3H), 8.16 (d, J=8.7 Hz, 2H), 7.80 (s, 1H), 7.73 (t, J=7.1 Hz, 1H), 7.11 (d, J=8.3 Hz, 1H), 7.02-6.86 (m, 1H). ESI-MS m/z 299.3 [M+H].

Step 2 Preparation of Compound 35

To a solution of compound 34 (27.98 g, 93.8 mmol) in 200 mL acetic acid was added iron powder (15.5 g, 281 mmol) in portions. Upon complete addition, the mixture was carefully heated to 100° C. After 3 h, the mixture was cooled to room temperature and filtered through Celite™. The Celite™ was washed with EtOH and the filtrate was concentrated under reduced pressure. The resulting residue was purified by column chromatography to give compound 35 of present invention in 88% yield. $^1$H NMR (400 MHz, DMSO) δ 11.25 (s, 1H), 8.29 (d, J=4.0 Hz, 1H), 7.77-7.60 (m, 1H), 7.57 (d, J=8.5 Hz, 2H), 7.09 (d, J=8.3 Hz, 1H), 6.99 (s, 1H), 6.94-6.79 (m, 1H), 6.58 (d, J=8.5 Hz, 2H), 5.18 (s, 2H). ESI-MS m/z 267.3 [M+11].

Step 3 Preparation of Compound 36

To a solution of compound 35 (133.2 mg, 0.5 mmol) in 5 mL pyridine was added acetyl chloride (58.9 mg, 0.75 mmol) at 0° C. After addition, the mixture was warmed to room temperature and stirred for 8 h until compound 35 was consumed. The mixture was then extracted, dried, evaporated and purified by column chromatography to give 132 mg of compound 36 in 85% yield. $^1$H NMR (400 MHz, DMSO) δ 11.37 (s, 1H), 9.99 (s, 1H), 8.30 (d, J=4.9 Hz, 1H), 7.82 (d, J=8.6 Hz, 2H), 7.70 (dd, J=11.2, 4.3 Hz, 1H), 7.62 (d, J=8.6 Hz, 2H), 7.29 (s, 1H), 7.09 (d, J=8.3 Hz, 1H), 7.00-6.84 (m, 1H), 2.06 (s, 3H). ESI-MS m/z 311.3 [M+H].

The following compounds were prepared using a procedure similar to that described above.

| No. | Structure | NMR/MS |
|---|---|---|
| 1 | 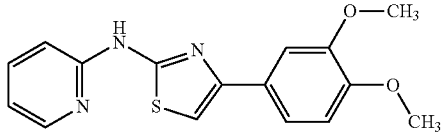 [SMILES: COc1ccc(-c2csc(Nc3ccccn3)n2)cc1OC] | ¹H NMR (400 MHz, CDCl₃) δ 9.84 (s, 1H), 8.34 (dd, J = 5.0, 1.0 Hz, 1H), 7.49-7.39 (m, 3H), 6.94 (s, 1H), 6.90-6.86 (m, 1H), 6.86-6.80 (m, 1H), 6.58 (d, J = 8.3 Hz, 1H), 3.92 (s, 3H), 3.86 (s, 3H). ESI-MS m/z 314.3 [M + H]. |
| 2 | 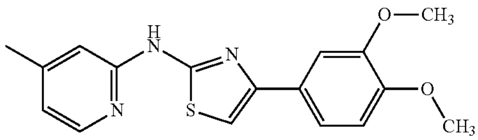 | ¹H NMR (400M, DMSO) δ 11.42 (br, 1H), 8.21 (d, J = 5.49 Hz, 1H), 7.49 (s, 1H), 7.46-7.39 (m, 1H), 7.31 (s, 1H), 6.98 (d, J = 8.2 Hz, 1H), 6.93 (s, 1H), 6.83 (d, J = 4.9 Hz, 1H), 3.98 (s, 3H), 3.90 (s, 3H), 2.39 (s, 3H). ESI-MS m/z 328.3 [M + H]. |
| 3 | 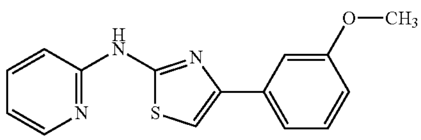 [SMILES: COc1cccc(-c2csc(Nc3ccccn3)n2)c1] | ¹H NMR (400 MHz, CDCl₃) δ 9.86 (s, 1H), 8.39-8.31 (m, 1H), 7.49-7.39 (m, 3H), 6.94 (s, 1H), 6.90-6.86 (m, 1H), 6.86-6.80 (m, 2H), 6.58 (d, J = 8.3 Hz, 1H), 3.86 (s, 3H). ESI-MS m/z 284.3 [M + H]. |
| 4 | 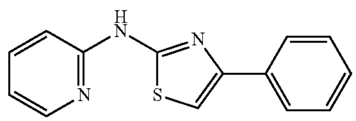 | ¹H NMR (400 MHz, CDCl₃) δ 9.89 (s, 1H), 8.27 (d, J = 5.0 Hz, 1H), 7.86-7.79 (m, 2H), 7.41-7.29 (m, 4H), 6.98 (s, 1H), 6.85-6.79 (m, 1H), 6.51 (d, J = 8.0 Hz, 1 H). ESI-MS m/z 254.3 [M + H]. |
| 5 | 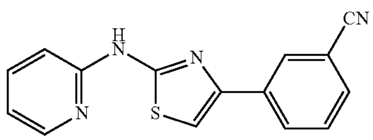 [SMILES: N#Cc1cccc(-c2csc(Nc3ccccn3)n2)c1] | ¹H NMR (400 MHz, CDCl3) δ 9.87 (s, 1H), 8.38-8.30 (m, 1H), 7.49-7.39 (m, 3H), 6.98 (s, 1H), 6.90-6.86 (m, 1H), 6.83-6.79 (m, 2H), 6.59 (d, J = 8.3 Hz, 1H). ESI-MS m/z 279.3 [M + H]. |
| 6 | 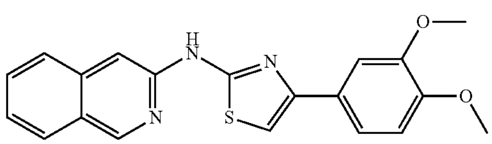 [SMILES: COc1ccc(-c2csc(Nc3cc4ccccc4cn3)n2)cc1OC] | ESI-MS m/z 365.3 [M + H]. |
| 7 | 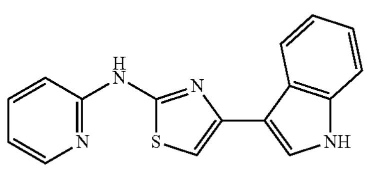 [SMILES: c1ccc(Nc2nc(-c3c[nH]c4ccccc34)cs2)nc1] | ESI-MS m/z 293.3 [M + H]. |
| 8 | 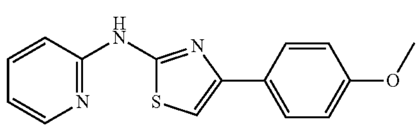 [SMILES: COc1ccc(-c2csc(Nc3ccccn3)n2)cc1] | ESI-MS m/z 284.3 [M + H]. |
| 9 | 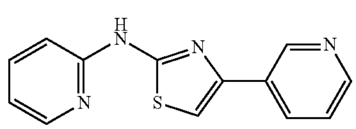 [SMILES: c1ccc(Nc2nc(-c3cccnc3)cs2)nc1] | ESI-MS m/z 255.3 [M + H]. |
| 10 | 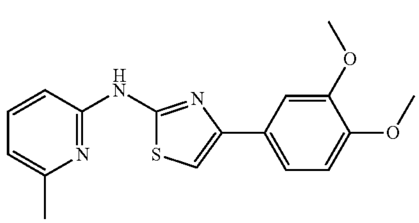 [SMILES: COc1ccc(-c2csc(Nc3cccc(C)n3)n2)cc1OC] | ¹H NMR (400 MHz, CDCl₃) δ 10.55 (s, 1H), 7.66-7.59 (m, 1H), 7.38 (d, J = 8.4 Hz, 1H), 7.34 (s, 1H), 7.03 (s, 1H), 6.97 (d, J = 8.4 Hz, 1H), 6.91 (d, J = 8.3 Hz, 1H), 6.89-6.81 (m, 1H), 3.97 (s, 3H), 3.91 (s, 3H), 2.41 (s, 3H). ESI-MS m/z 328.3 [M + H]. |

-continued
| No. | Structure | NMR/MS |
|---|---|---|
| 11 | 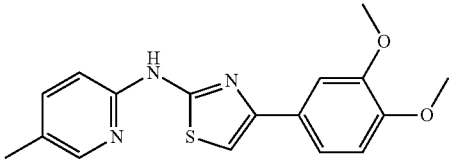 | $^1$H NMR (400M, DMSO) δ 11.39 (br, 1H), 8.18 (s, 1H), 7.61 (d, J = 8.2 Hz, 1H), 7.49-7.40 (m, 2H), 7.34 (s, 1H), 7.01 (d, J = 8.2 Hz, 1H), 6.98 (d, J = 8.2 Hz, 1H), 3.91 (s, 3H), 3.88 (s, 3H), 2.34 (s, 3H). ESI-MS m/z 328.3 [M + H]. |
| 12 | 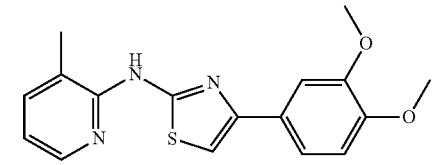 [SMILES: COc1ccc(-c2csc(Nc3ncccc3C)n2)cc1OC] | ESI-MS m/z 328.3 [M + H]. |
| 13 | 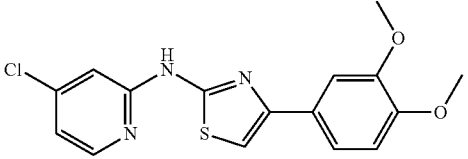 [SMILES: COc1ccc(-c2csc(Nc3cc(Cl)ccn3)n2)cc1OC] | ESI-MS m/z 348.9 [M + H]. |
| 14 | 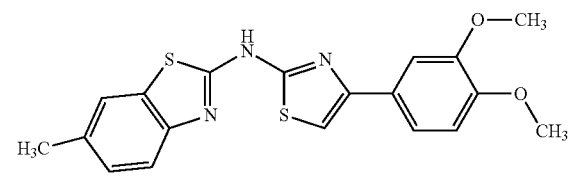 | ESI-MS m/z 384.3 [M + H]. |
| 15 | 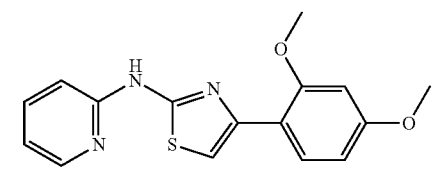 [SMILES: COc1ccc(-c2csc(Nc3ccccn3)n2)c(OC)c1] | ESI-MS m/z 314.3 [M + H]. |
| 16 | 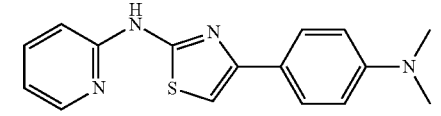 [SMILES: CN(C)c1ccc(-c2csc(Nc3ccccn3)n2)cc1] | ESI-MS m/z 297.3 [M + H]. |
| 17 | 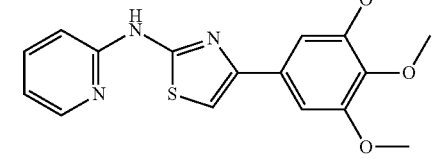 | ESI-MS m/z 344.3 [M + H]. |
| 18 | 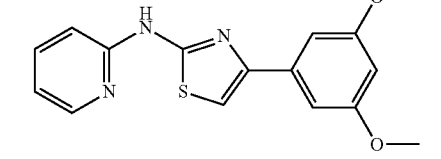 | $^1$H NMR (400 MHz, CDCl$_3$) δ 9.88 (s, 1H), 8.46-8.09 (m, 1H), 7.47-7.32 (m, 3H), 7.16 (s, 1H), 6.98 (d, J = 2.4 Hz, 2H), 6.49 (d, J = 2.4 Hz, 1H), 3.94 (s, 3H), 3.82 (s, 3H). ESI-MS m/z 314.3 [M + H]. |
| 19 | 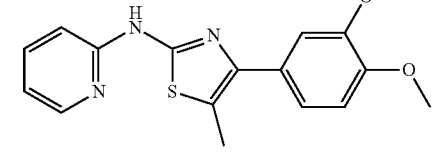 | ESI-MS m/z 328.3 [M + H]. |

-continued

| No. | Structure | NMR/MS |
|---|---|---|
| 20 | 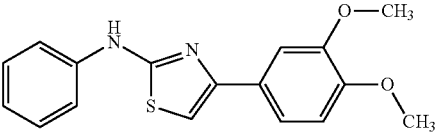 [SMILES: COc1ccc(-c2csc(Nc3ccccc3)n2)cc1OC] | ¹H NMR (400 MHz, CDCl₃) δ 7.52 (s, 1H), 7.41 (d, J = 6.9 Hz, 2H), 7.36 (dd, J = 8.6, 5.7 Hz, 4H), 7.13-7.04 (m, 1H), 6.90 (d, J = 8.9 Hz, 1H), 6.71 (s, 1H), 3.95 (s, 3H), 3.92 (s, 3H). ESI-MS m/z 313.3 [M + H]. |
| 21 | 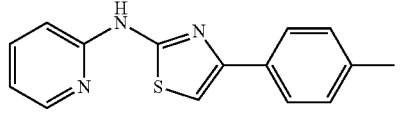 [SMILES: Cc1ccc(-c2csc(Nc3ccccn3)n2)cc1] | ¹H NMR (400 MHz, CDCl₃) δ 10.11 (s, 1H), 8.33 (d, J = 4.5 Hz, 1H), 7.78 (d, J = 7.8 Hz, 2H), 7.39 (d, J = 6.1 Hz, 1H), 7.19 (d, J = 7.8 Hz, 2H), 6.99 (s, 1H), 6.82 (d, J = 5.1 Hz, 1H), 6.54 (s, 1H), 2.39 (s, 3H). ESI-MS m/z 268.3 [M + H]. |
| 22 | 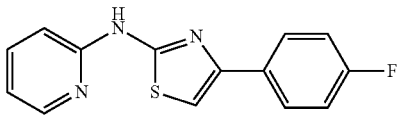 [SMILES: Fc1ccc(-c2csc(Nc3ccccn3)n2)cc1] | ¹H NMR (400 MHz, CDCl₃) δ 9.83 (s, 1H), 8.34 (d, J = 4.6 Hz, 1H), 7.85 (dd, J = 8.7, 5.5 Hz, 2H), 7.44 (t, J = 7.7 Hz, 1H), 7.07 (t, J = 8.6 Hz, 2H), 6.97 (s, 1H), 6.89-6.79 (m, 1H), 6.58 (d, J = 5.7 Hz, 1H). ESI-MS m/z 272.3 [M + H]. |
| 23 | 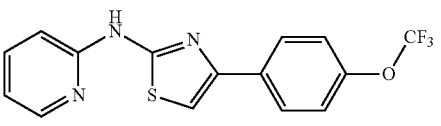 [SMILES: FC(F)(F)Oc1ccc(-c2csc(Nc3ccccn3)n2)cc1] | ¹H NMR (400 MHz, CDCl₃) δ 10.19 (s, 1H), 8.33 (t, J = 7.5 Hz, 1H), 7.90 (d, J = 8.6 Hz, 2H), 7.38 (t, J = 7.8 Hz, 1H), 7.21 (d, J = 8.4 Hz, 2H), 7.04 (s, 1H), 6.87-6.76 (m, 1H), 6.47 (d, J = 8.3 Hz, 1H). ESI-MS m/z 338.3 [M + H]. |
| 24 | 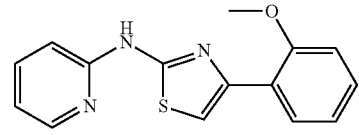 [SMILES: COc1ccccc1-c1csc(Nc2ccccn2)n1] | ¹H NMR (400 MHz, CDCl₃) δ 9.33 (s, 1H), 8.35 (d, J = 4.5 Hz, 1H), 8.13 (d, J = 7.6 Hz, 1H), 7.54-7.39 (m, 2H), 7.27 (d, J = 11.3 Hz, 1H), 7.01 (t, J = 8.0 Hz, 2H), 6.90-6.79 (m, 1H), 6.73 (d, J = 8.3 Hz, 1H), 3.97 (s, 3H). ESI-MS m/z 283.3 [M + H]. |
| 25 | 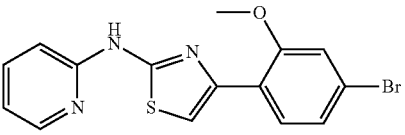 [SMILES: COc1cc(Br)ccc1-c1csc(Nc2ccccn2)n1] | ¹H NMR (400 MHz, CDCl₃) δ 9.36 (s, 1H), 8.35 (d, J = 4.5 Hz, 1H), 8.13 (d, J = 7.6 Hz, 1H), 7.54-7.39 (m, 2H), 7.27 (d, J = 11.3 Hz, 1H), 7.01 (t, J = 8.0 Hz, 2H), 6.90-6.79 (m, 1H), 6.73 (d, J = 8.3 Hz, 1H), 3.97 (s, 3H). ESI-MS m/z 363.3 [M + H]. |
| 26 | 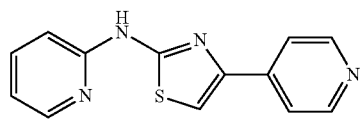 [SMILES: c1ccc(Nc2nc(-c3ccncc3)cs2)nc1] | ¹H NMR (400 MHz, CDCl₃) δ 9.20 (s, 1H), 8.63 (d, J = 5.1 Hz, 2H), 8.37 (d, J = 3.9 Hz, 1H), 7.75 (d, J = 5.0 Hz, 2H), 7.56 (t, J = 7.2 Hz, 1H), 7.29 (s, 1H), 6.99-6.81 (m, 1H), 6.74 (d, J = 8.2 Hz, 1H). ESI-MS m/z 255.3 [M + H]. |
| 27 | 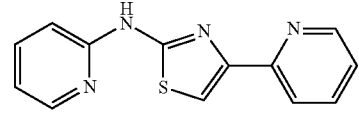 [SMILES: c1ccc(Nc2nc(-c3ccccn3)cs2)nc1] | ¹H NMR (400 MHz, CDCl₃) δ 9.44 (s, 1H), 8.63 (d, J = 4.5 Hz, 1H), 8.36 (d, J = 4.8 Hz, 1H), 7.97 (d, J = 7.9 Hz, 1H), 7.70 (t, J = 7.7 Hz 1H) 7.61 (s, 1H) 7.51 (dd, J = 11.1, 4.4 Hz, 1H), 7.22-7.14 (m, 1H), 6.93-6.83 (m, 1H), 6.72 (d, J = 8.3 Hz, 1H). ESI-MS m/z 255.3 [M + H]. |

-continued

| No. | Structure | NMR/MS |
|---|---|---|
| 28 | 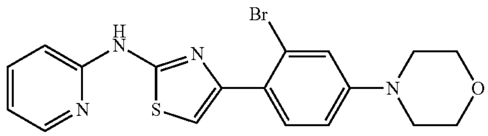 [SMILES: Brc1cc(N2CCOCC2)ccc1-c1csc(Nc2ccccn2)n1] | $^1$H NMR (400 MHz, DMSO) δ 11.40 (s, 1H), 8.30 (d, J = 4.6 Hz, 1H), 8.16 (s, 1H), 7.87 (d, J = 8.2 Hz, 1H), 7.71 (t, J = 7.4 Hz, 1H), 7.43 (s, 1H), 7.20 (d, J = 8.3 Hz, 1H), 7.08 (d, J = 8.3 Hz, 1H), 7.04-6.78 (m, 1H), 3.76 (s, 4H), 3.00 (s, 4H). ESI-MS m/z 418.3 [M + H]. |
| 29 | 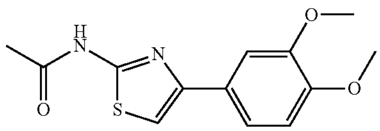 [SMILES: COc1ccc(-c2csc(NC(C)=O)n2)cc1OC] | $^1$H NMR (400 MHz, CDCl$_3$) δ 10.55 (s, 1H), 7.38 (d, J = 8.4 Hz, 1H), 7.34 (s, 1H), 7.03 (s, 1H), 6.91 (d, J = 8.3 Hz, 1H), 3.98 (s, 3H), 3.87 (s, 3H), 2.00 (s, 3H). ESI-MS m/z 279.3 [M + H]. |
| 30 | 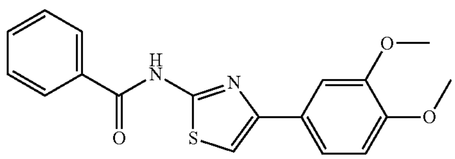 [SMILES: COc1ccc(-c2csc(NC(=O)c3ccccc3)n2)cc1OC] | $^1$H NMR (400 MHz, CDCl$_3$) δ 7.98 (d, J = 7.6 Hz, 2H), 7.61 (t, J = 7.5 Hz, 1H), 7.53 (t, J = 7.6 Hz, 2H), 7.38 (t, J = 7.4 Hz, 2H), 7.08 (s, 1H), 6.91 (d, J = 8.0 Hz, 1H), 3.96 (s, 3H), 3.92 (s, 3H). ESI-MS m/z 341.3 [M + H]. |
| 31 | 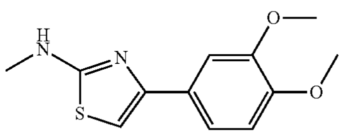 | $^1$H NMR (400 MHz, CDCl$_3$) δ 7.38 (s, 1H), 7.34 (d, J = 8.2 Hz, 1H), 6.78 (d, J = 8.3 Hz, 1H), 6.00 (s, 1H), 3.90 (d, J = 4.9 Hz, 6H), 2.88 (s, 3H). ESI-MS m/z 251.3 [M + H]. |
| 32 | 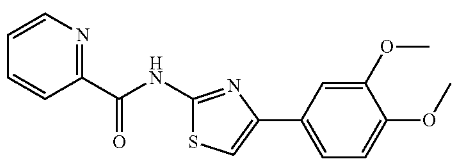 [SMILES: COc1ccc(-c2csc(NC(=O)c3ccccn3)n2)cc1OC] | $^1$H NMR (400 MHz, CDCl$_3$) δ 11.23 (s, 1H), 8.69 (d, J = 4.8 Hz, 1H), 8.31 (d, J = 7.8 Hz, 1H), 7.96 (t, J = 7.0 Hz, 1H), 7.55 (dd, J = 7.4, 5.0 Hz, 1H), 7.47 (s, 1H), 7.46-7.41 (m, 1H), 7.11 (s, 1H), 6.93 (d, J = 8.3 Hz, 1H), 3.99 (s, 3H), 3.93 (s, 3H). ESI-MS m/z 342.3 [M + H]. |
| 33 | 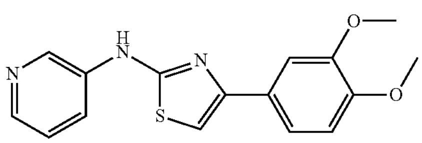 [SMILES: COc1ccc(-c2csc(Nc3cccnc3)n2)cc1OC] | $^1$H NMR (400 MHz, DMSO) δ 10.45 (s, 1H), 8.84 (d, J = 2.5 Hz, 1H), 8.27 (d, J = 9.4 Hz, 1H), 8.17 (d, J = 3.4 Hz, 1H), 7.59-7.45 (m, 2H), 7.38 (dd, J = 8.3, 4.6 Hz, 1H), 7.29 (s, 1H), 7.02 (d, J = 8.4 Hz, 1H), 3.84 (s, 3H), 3.79 (s, 3H). ESI-MS m/z 314.3 [M + H] |
| 34 | 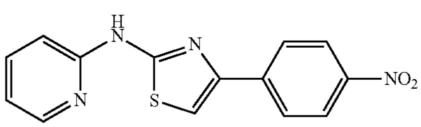 [SMILES: Nc1ccc(-c2csc(Nc3ccccn3)n2)cc1] | $^1$H NMR (400 MHz, DMSO) δ 11.53 (s, 1H), 8.30 (dd, J = 12.9, 6.7 Hz, 3H), 8.16 (d, J =8.7 Hz, 2H), 7.80 (s, 1H), 7.73 (t, J = 7.1 Hz, 1H), 7.11 (d, J = 8.3 Hz, 1H), 7.02-6.86 (m, 1H). ESI-MS m/z 299.3 [M + H]. |
| 35 | 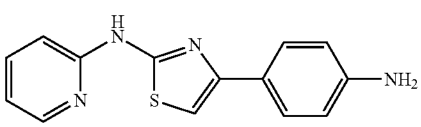 | $^1$H NMR (400 MHz, DMSO) δ 11.25 (s, 1H), 8.29 (d, J = 4.0 Hz, 1H), 7.77-7.60 (m, 1H), 7.57 (d, J = 8.5 Hz, 2H), 7.09 (d, J = 8.3 Hz, 1H), 6.99 (s, 1H), 6.94-6.79 (m, 1H), 6.58 (d, J = 8.5 Hz, 2H), 5.18 (s, 2H). ESI-MS m/z 267.3 [M + H]. |
| 36 | 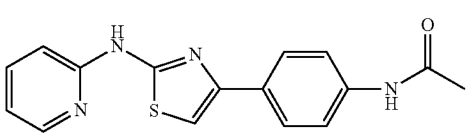 [SMILES: CC(=O)Nc1ccc(-c2csc(Nc3ccccn3)n2)cc1] | $^1$H NMR (400 MHz, DMSO) δ 11.37 (s, 1H), 9.99 (s, 1H), 8.30 (d, J = 4.9 Hz, 1H), 7.82 (d, J = 8.6 Hz, 2H), 7.70 (dd, J = 11.2, 4.3 Hz, 1H), 7.62 (d, J = 8.6 Hz, 2H), 7.29 (s, 1H), 7.09 (d, J = 8.3 Hz, 1H), 7.00-6.84 (m, 1H), 2.06 |

| No. | Structure | NMR/MS |
|---|---|---|
| | | (s, 3H). ESI-MS m/z 311.3 [M + H]. |
| 37 | 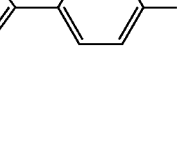 | ¹H NMR (400 MHz, DMSO) δ 11.35 (s, 1H), 8.35 (s, 1H), 8.30 (d, J = 4.7 Hz, 1H), 7.76 (d, J = 8.5 Hz, 2H), 7.70 (t, J = 7.8 Hz, 1H), 7.42 (d, J = 8.5 Hz, 2H), 7.22 (s, 1H), 7.09 (d, J = 8.3 Hz, 1H), 6.99-6.84 (m, 1H), 6.02 (d, J = 7.5 Hz, 1H), 3.76 (dd, J = 13.4, 6.7 Hz, 1H), 1.10 (d, J = 6.5 Hz, 6H). ESI-MS m/z 354.3 [M + H]. |
| 38 | 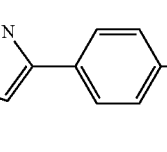 | ¹H NMR (400 MHz, DMSO) δ 11.37 (s, 1H), 9.92 (s, 1H), 8.30 (d, J = 4.0 Hz, 1H), 7.79 (t, J = 21.9 Hz, 2H), 7.77-7.67 (m, 1H), 7.64 (d, J = 8.7 Hz, 2H), 7.29 (s, 1H), 7.09 (d, J = 8.3 Hz, 1H), 6.98-6.85 (m, 1H), 2.33 (q, J = 7.5 Hz, 2H), 1.10 (t, J = 7.5 Hz, 3H). ESI-MS m/z 325.3 [M + H]. |
| 39 | 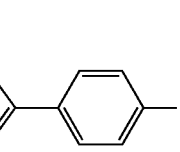 | ¹H NMR (400 MHz, DMSO) δ 11.37 (s, 1H), 9.92 (s, 1H), 8.44-8.21 (m, 1H), 7.83 (d, J = 8.7 Hz, 2H), 7.75-7.67 (m, 1H), 7.65 (d, J = 8.7 Hz, 2H), 7.29 (s, 1H), 7.09 (d, J = 8.3 Hz, 1H), 6.92 (dd, J = 6.8, 5.5 Hz, 1H), 2.30 (t, J = 7.3 Hz, 2H), 1.62 (dd, J = 14.7, 7.4 Hz, 2H), 0.93 (t, J = 7.4 Hz, 3H). ESI-MS m/z 339.3 [M + H]. |
| 40 | 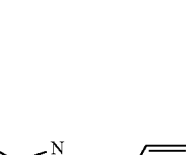 | ¹H NMR (400 MHz, DMSO) δ 11.42 (s, 1H), 8.31 (dd, J = 5.1, 1.1 Hz, 1H), 7.89-7.84 (m, 2H), 7.75-7.69 (m, 1H), 7.64-7.59 (m, 2H), 7.50 (s, 1H), 7.09 (d, J = 8.4 Hz, 1H), 6.96-6.91 (m, 1H). ESI-MS m/z 333.1 [M + H]. |
| 41 | 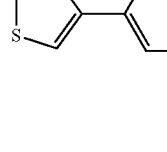 | ¹H NMR (400 MHz, DMSO-d₆) δ 11.63 (s, 1H), 8.35 (d, J = 4.2 Hz, 1H), 7.81 (t, J = 7.3 Hz, 1H), 7.74 (d, J = 8.7 Hz, 2H), 7.22 (s, 1H), 7.18 (d, J = 8.4 Hz, 1H), 7.01(t, J = 6.4 Hz, 1H), 6.81 (d, J = 8.7 Hz, 2H). ESI-MS m/z 270.3 [M + H]. |
| 42 | 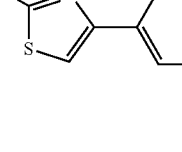 | ¹H NMR (400 MHz, DMSO-d₆) δ 11.34 (s, 1H), 8.30 (dd, J = 5.0, 1.1 Hz, 1H), 7.81 (d, J = 8.8 Hz, 2H), 7.70 (ddd, J = 8.8, 7.3, 1.9 Hz, 1H), 7.23 (s, 1H), 7.10 (d, J = 8.4 Hz, 1H), 6.94 (d, J = 8.8 Hz, 2H), 6.92-6.89 (m, 1H), 4.64 (dt, J = 12.0, 6.0 Hz, 1H), 1.28 (d, J = 6.0 Hz, 6H). ESI-MS m/z 312.3 [M + H]. |
| 43 | 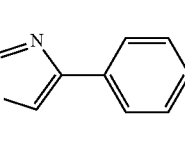 | ¹H NMR (400 MHz, DMSO-d₆) δ 11.34 (s, 1H), 8.30 (dd, J = 5.1, 1.1 Hz, 1H), 7.82 (d, J = 8.8 Hz, 2H), 7.70 (ddd, J = 8.8, 7.2, 1.9 Hz, 1H), 7.24 (s, 1H), 7.09 (d, J = 8.4 Hz, 1H), 6.96 (d, J = 8.9 Hz, 2H), 6.90 (d, J = 0.8 Hz, 1H), 4.00 (t, J = 6.5 Hz, 2H), 1.76-1.65 (m, 2H), 1.51-1.38 (m, 2H), 0.94 (t, J = 7.4 Hz, 3H). ESI-MS m/z 326.3 [M + H]. |

| No. | Structure | NMR/MS |
|---|---|---|
| 44 | 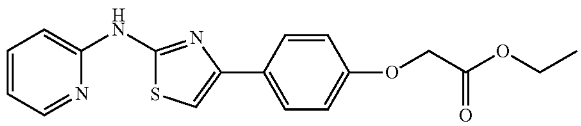 [SMILES: CCOC(=O)COc1ccc(-c2csc(Nc3ccccn3)n2)cc1] | $^1$H NMR (400 MHz, DMSO-d$_6$) δ 11.35 (s, 1H), 8.30 (dd, J = 5.1, 1.1 Hz, 1H), 7.83 (d, J = 8.8 Hz, 2H), 7.70 (ddd, J = 8.8, 7.2, 1.9 Hz, 1H), 7.27 (s, 1H), 7.10 (d, J = 8.3 Hz, 1H), 6.97 (d, J = 8.9 Hz, 2H), 6.92 (dd, J = 6.7, 5.5 Hz, 1H), 4.81 (s, 2H), 4.18 (q, J = 7.1 Hz, 2H), 1.22 (t, J = 7.1 Hz, 3H). ESI-MS m/z 356.3 [M + H]. |
| 45 | 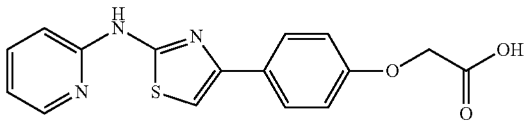 [SMILES: O=C(O)COc1ccc(-c2csc(Nc3ccccn3)n2)cc1] | $^1$H NMR (400 MHz, DMSO) δ 13.01 (s, 1H), 11.37 (s, 1H), 8.30 (d, J = 4.0 Hz, 1H), 7.83 (d, J = 8.8 Hz, 2H), 7.76-7.67 (m, 1H), 7.26 (s, 1H), 7.10 (d, J = 8.3 Hz, 1H), 6.96 (d, J = 8.8 Hz, 2H), 6.92 (dd, J = 6.9, 5.7 Hz, 1H), 4.71 (s, 2H). ESI-MS m/z 328.3 [M + H]. |
| 46 | 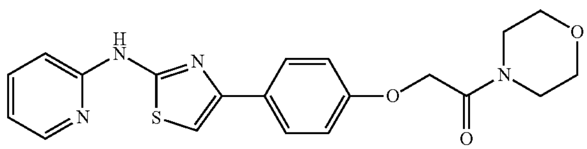 [SMILES: O=C(COc1ccc(-c2csc(Nc3ccccn3)n2)cc1)N1CCOCC1] | $^1$H NMR (400 MHz, DMSO) δ 11.35 (s, 1H), 8.30 (dd, J = 5.1, 1.1 Hz, 1H), 7.82 (d, J = 8.8 Hz, 2H), 7.70 (ddd, J = 8.9, 5.4, 1.9 Hz, 1H), 7.26 (s, 1H), 7.10 (d, J = 8.4 Hz, 1H), 7.00-6.94 (m, 2H), 6.95-6.89 (m, 1H), 4.86 (s, 2H), 3.66-3.53 (m, 4H), 3.47 (s, 4H). ESI-MS m/z 397.4 [M + H]. |
| 47 | 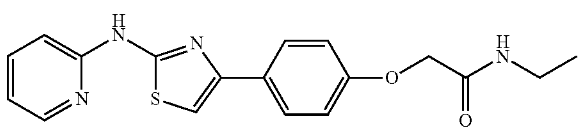 [SMILES: CCNC(=O)COc1ccc(-c2csc(Nc3ccccn3)n2)cc1] | $^1$H NMR (400 MHz, DMSO) δ 9.49 (s, 1H), 8.41 (d, J = 3.7 Hz, 1H), 8.26 (t, J = 5.5 Hz, 1H), 7.82 (dt, J = 8.9, 5.4 Hz, 1H), 7.75 (d, J = 8.6 Hz, 2H), 7.22 (s, 1H), 7.15 (d, J = 8.6 Hz, 1H), 7.05 (dd, J = 7.0, 5.0 Hz, 1H), 6.78 (d, J = 8.6 Hz, 2H), 5.02 (s, 2H), 3.20-3.07 (m, 2H), 1.06 (t, J = 7.2 Hz, 3H). ESI-MS m/z 355.3 [M + H]. |
| 48 | 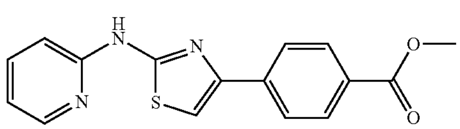 [SMILES: COC(=O)c1ccc(-c2csc(Nc3ccccn3)n2)cc1] | $^1$H NMR (400 MHz, DMSO) δ 11.50 (s, 1H), 8.32 (d, J = 4.4 Hz, 1H), 8.04 (q, J = 8.6 Hz, 4H), 7.74 (t, J = 7.0 Hz, 1H), 7.66 (s, 1H), 7.11 (d, J = 8.4 Hz, 1H), 6.98-6.93 (m, 1H), 3.87 (s, 3H). ESI-MS m/z 312.3 [M + H]. |
| 49 | 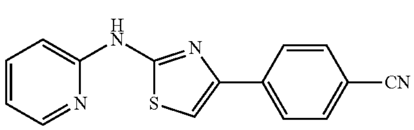 [SMILES: N#Cc1ccc(-c2csc(Nc3ccccn3)n2)cc1] | $^1$H NMR (400 MHz, DMSO) δ 11.51 (s, 1H), 8.32 (dd, J = 5.1, 1.1 Hz, 1H), 8.10 (d, J = 8.5 Hz, 2H), 7.93-7.85 (m, 2H), 7.79-7.71 (m, 2H), 7.12 (d, J = 8.3 Hz, 1H), 6.96 (dd, J = 6.7, 5.5 Hz, 1H). ESI-MS m/z 279.3 [M + H]. |
| 50 | 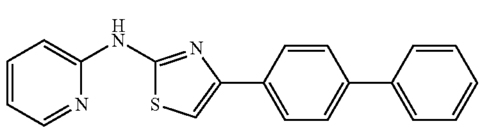 [SMILES: c1ccc(-c2ccc(-c3csc(Nc4ccccn4)n3)cc2)cc1] | $^1$H NMR (400 MHz, DMSO) δ 11.59 (s, 1H), 8.35 (d, J = 4.3 Hz, 1H), 8.02 (d, J = 8.3 Hz, 2H), 7.82-7.69 (m, 5H), 7.53 (s, 1H), 7.48 (t, J = 7.6 Hz, 2H), 7.37 (t, J = 7.3 Hz, 1H), 7.16 (d, J = 8.3 Hz, 1H), 7.03-6.96 (m, 1H). ESI-MS m/z 330.3 [M + H]. |
| 51 | 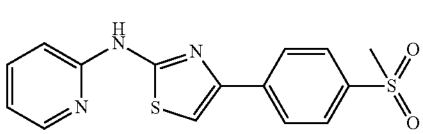 [SMILES: CS(=O)(=O)c1ccc(-c2csc(Nc3ccccn3)n2)cc1] | $^1$H NMR (400 MHz, DMSO) δ 11.57 (s, 1H), 8.33 (dd, J = 5.1, 1.1 Hz, 1H), 8.22-8.14 (m, 2H), 7.97 (d, J = 8.6 Hz, 2H), 7.79-7.71 (m, 2H), 7.12 (d, J = 8.4 Hz, 1H), 6.97 (dd, J = 6.5, 5.2 Hz, 1H), 3.24 (s, 3H). ESI-MS m/z 332.4 [M + H]. |

-continued

| No. | Structure | NMR/MS |
|---|---|---|
| 52 | 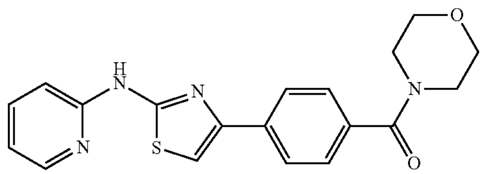 [SMILES: O=C(c1ccc(-c2csc(Nc3ccccn3)n2)cc1)N1CCOCC1] | ¹H NMR (400 MHz, DMSO) δ 11.43 (s, 1H), 8.32 (d, J = 4.0 Hz, 1H), 7.97 (t, J = 6.3 Hz, 2H), 7.77-7.68 (m, 1H), 7.54 (s, 1H), 7.47 (d, J = 8.3 Hz, 2H), 7.11 (d, J = 8.3 Hz, 1H), 6.95 (dd, J = 6.7, 5.5 Hz, 1H), 3.61-3.49 (m, 8H). ESI-MS m/z 367.3 [M + H]. |
| 53 | 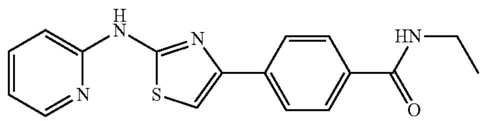 [SMILES: CCNC(=O)c1ccc(-c2csc(Nc3ccccn3)n2)cc1] | ¹H NMR (400 MHz, DMSO) δ 11.44 (s, 1H), 8.47 (t, J = 5.4 Hz, 1H), 8.32 (d, J = 4.0 Hz, 1H), 7.99 (d, J = 8.4 Hz, 2H), 7.90 (d, J = 8.5 Hz, 2H), 7.76-7.69 (m, 1H), 7.58 (s, 1H), 7.11 (d, J = 8.3 Hz, 1H), 6.95 (dd, J = 6.7, 5.5 Hz, 1H), 1.14 (t, J = 7.2 Hz, 3H). ESI-MS m/z 325.3 [M + H]. |
| 54 | 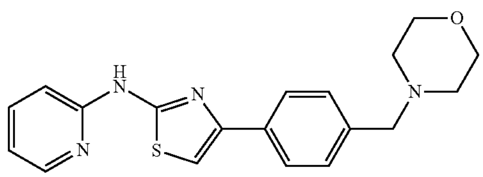 [SMILES: c1ccc(Nc2nc(-c3ccc(CN4CCOCC4)cc3)cs2)nc1] | ¹H NMR (400 MHz, CDCl₃) δ 8.77 (s, 1H), 8.34 (d, J = 4.9 Hz, 1H), 7.82 (d, J = 8.2 Hz, 2H), 7.58-7.50 (m, 1H), 7.36 (d, J = 8.2 Hz, 2H), 7.01 (s, 1H), 6.90-6.83 (m, 1H), 6.77 (d, J = 8.3 Hz, 1H), 3.78-3.69 (m, 4H), 3.57 (s, 2H), 2.51 (s, 4H). ESI-MS m/z 353.4 [M + H]. |
| 55 | 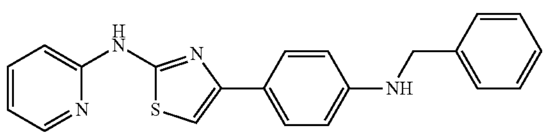 [SMILES: c1ccc(CNc2ccc(-c3csc(Nc4ccccn4)n3)cc2)cc1] | ¹H NMR (400 MHz, DMSO) δ 11.25 (s, 1H), 8.28 (d, J = 4.0 Hz, 1H), 7.72-7.63 (m, 1H), 7.60 (d, J = 8.6 Hz, 2H), 7.41-7.33 (m, 4H), 7.29-7.17 (m, 1H), 7.08 (d, J = 8.4 Hz, 1H), 7.00 (s, 1H), 6.90 (dd, J = 6.6, 5.6 Hz, 1H), 6.61 (d, J = 8.7 Hz, 2H), 6.38 (t, J = 6.0 Hz, 1H), 4.31 (d, J = 6.0 Hz, 2H). ESI-MS m/z 359.3 [M + H]. |
| 56 | 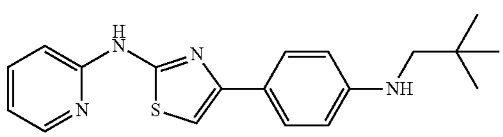 [SMILES: CC(C)(C)CNc1ccc(-c2csc(Nc3ccccn3)n2)cc1] | ¹H NMR (400 MHz, DMSO) δ 11.26 (s, 1H), 8.29 (d, J = 4.1 Hz, 1H), 7.74-7.63 (m, 1H), 7.61 (d, J = 8.6 Hz, 2H), 7.08 (d, J = 8.3 Hz, 1H), 6.99 (s, 1H), 6.94-6.84 (m, 1H), 6.66 (d, J = 8.7 Hz, 2H), 5.58 (t, J = 6.0 Hz, 1H), 2.85 (d, J = 6.0 Hz, 2H), 0.96 (s, 9H). ESI-MS m/z 339.3 [M + H]. |
| 57 | 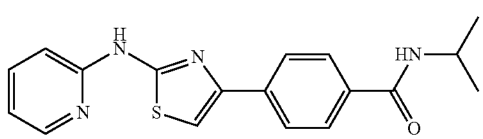 [SMILES: CC(C)NC(=O)c1ccc(-c2csc(Nc3ccccn3)n2)cc1] | ¹H NMR (400 MHz, DMSO) δ 11.44 (s, 1H), 8.31 (d, J = 4.0 Hz, 1H), 8.21 (d, J = 7.6 Hz, 1H), 7.98 (d, J = 8.4 Hz, 2H), 7.90 (d, J = 8.4 Hz, 2H), 7.78-7.64 (m, 1H), 7.57 (s, 1H), 7.10 (d, J = 8.3 Hz, 1H), 7.00-6.82 (m, 1H), 4.11 (dd, J = 14.0, 6.7 Hz, 1H), 1.18 (d, J = 6.6 Hz, 6H). ESI-MS m/z 339.3 [M + H]. |
| 58 | 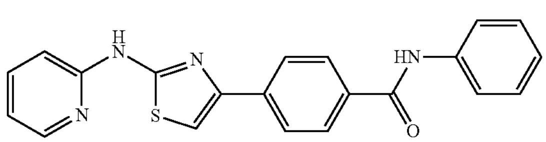 [SMILES: O=C(Nc1ccccc1)c1ccc(-c2csc(Nc3ccccn3)n2)cc1] | ¹H NMR (400 MHz, DMSO) δ 11.47 (s, 1H), 10.25 (s, 1H), 8.32 (d, J = 4.1 Hz, 1H), 8.09-8.02 (m, 4H), 7.80 (d, J = 8.3 Hz, 2H), 7.73 (t, J = 7.7 Hz, 1H), 7.64 (s, 1H), 7.36 (t, J = 7.9 Hz, 2H), 7.23-7.03 (m, 2H), 6.99-6.83 (m, 1H). ESI-MS m/z 373.3 [M + H]. |

| No. | Structure | NMR/MS |
|---|---|---|
| 59 | 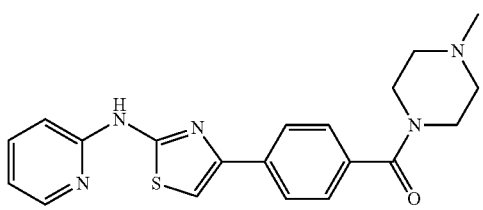 [SMILES: CN1CCN(C(=O)c2ccc(-c3csc(Nc4ccccn4)n3)cc2)CC1] | ¹H NMR (400 MHz, DMSO) δ 11.43 (s, 1H), 8.50-8.13 (m, 1H), 7.97 (d, J = 8.2 Hz, 2H), 7.81-7.64 (m, 1H), 7.51 (s, 1H), 7.43 (d, J = 8.3 Hz, 2H), 7.11 (d, J = 8.3 Hz, 1H), 6.93 (dd, J = 6.6, 5.4 Hz, 1H), 3.66-3.57 (br, 4H), 2.44-2.35 (br, 4H), 2.19 (s, 3H). ESI-MS m/z 380.3 [M + H]. |
| 60 | 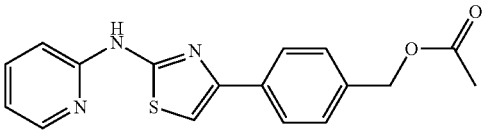 [SMILES: CC(=O)OCc1ccc(-c2csc(Nc3ccccn3)n2)cc1] | ESI-MS m/z 326.3 [M + H]. |
| 61 | 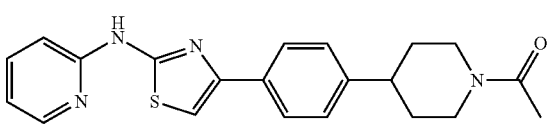 [SMILES: CC(=O)N1CCC(c2ccc(-c3csc(Nc4ccccn4)n3)cc2)CC1] | ¹H NMR (400 MHz, DMSO-d₆) δ 11.36 (s, 1H), 8.30 (dd, J = 4.8, 1.0 Hz, 1H), 7.84 (d, J = 8.3 Hz, 2H), 7.75-7.66 (m, 1H), 7.35 (s, 1H), 7.29 (d, J = 8.3 Hz, 2H), 7.10 (d, J = 8.4 Hz, 1H), 6.92 (dd, J = 6.7, 5.5 Hz, 1H), 4.59-4.49 (m, 1H), 3.92 (d, J = 13.4 Hz, 1H), 3.13 (t, J = 11.9 Hz, 1H), 2.78 (t, J = 12.0 Hz, 1H), 2.63-2.59 (m, 1H), 2.03 (s, 3H), 1.91-1.82 (m, 2H), 1.69-1.60 (m, 1H), 1.49-1.42 (m, 1H). ESI-MS m/z 379.3 [M + H]. |
| 62 | 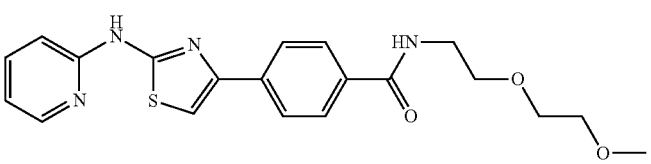 [SMILES: COCCOCCNC(=O)c1ccc(-c2csc(Nc3ccccn3)n2)cc1] | ¹H NMR (400 MHz, DMSO-d₆) δ 11.44 (s, 1H), 8.51 (t, J = 5.5 Hz, 1H), 8.31 (d, J = 4.0 Hz, 1H), 7.99 (d, J = 8.5 Hz, 2H), 7.90 (d, J = 8.5 Hz, 2H), 7.76-7.68 (m, 1H), 7.58 (s, 1H), 7.10 (d, J = 8.4 Hz, 1H), 6.97-6.90 (m, 1H), 3.59-3.50 (m, 4H), 3.48-3.39 (m, 4H), 3.24 (s, 3H). ESI-MS m/z 399.4 [M + H]. |
| 63 | 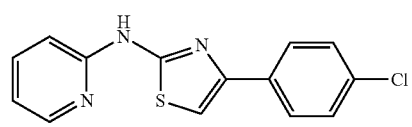 [SMILES: Clc1ccc(-c2csc(Nc3ccccn3)n2)cc1] | ¹H NMR (400 MHz, DMSO) δ 11.53 (s, 1H), 8.33 (d, J = 4.0 Hz, 1H), 7.94 (d, J = 8.6 Hz, 2H), 7.82-7.72 (m, 1H), 7.56-7.42 (m, 3H), 7.14 (d, J = 8.4 Hz, 1H), 7.04-6.89 (m, 1H). ESI-MS m/z 288.3 [M + H]. |
| 64 | 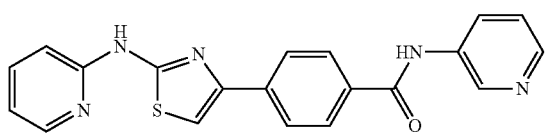 [SMILES: O=C(Nc1cccnc1)c1ccc(-c2csc(Nc3ccccn3)n2)cc1] | ¹H NMR (400 MHz, CDCl₃) δ 10.56 (s, 1H), 9.87 (s, 1H), 8.59 (d, J = 8.4 Hz, 1H), 8.46-8.39 (m, 2H), 7.85 (t, J = 7.9 Hz, 1H), 7.69-7.58 (m, 5H), 7.20-7.14 (m, 1H), 7.05 (s, 1H), 6.95-6.91 (m, 1H), 6.87 (d, J = 8.2 Hz, 1H). ESI-MS m/z 374.4 [M + H]. |
| 65 | 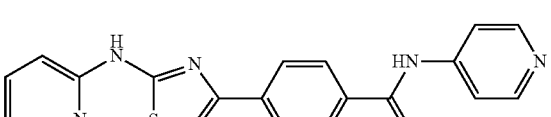 | ¹H NMR (400 MHz, DMSO) δ 11.47 (s, 1H), 10.59 (s, 1H), 8.49 (d, J = 6.2 Hz, 2H), 8.32 (d, J = 4.1 Hz, 1H), 8.07 (q, J = 8.5 Hz, 4H), 7.81 (d, J = 6.3 Hz, 2H), 7.72 (dd, J = 11.3, 4.2 Hz, 1H), 7.66 (s, 1H), 7.11 (d, J = 8.4 Hz, 1H), 6.98-6.92 (m, 1H). ESI-MS m/z 374.4 [M + H]. |

-continued

| No. | Structure | NMR/MS |
|---|---|---|
| 66 | 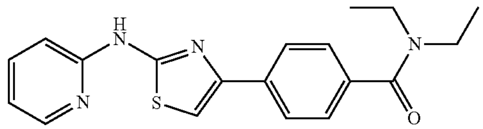 [SMILES: CCN(CC)C(=O)c1ccc(-c2csc(Nc3ccccn3)n2)cc1] | ESI-MS m/z 353.4 [M + H]. |
| 67 | 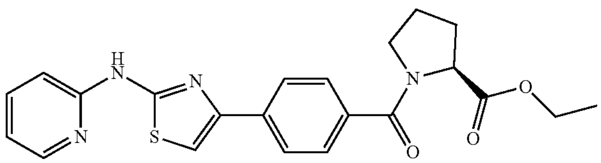 | ESI-MS m/z 443.4 [M + H]. |
| 68 | 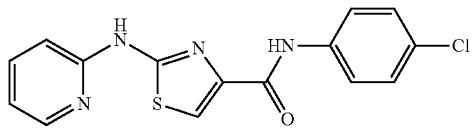 [SMILES: O=C(Nc1ccc(Cl)cc1)c1csc(Nc2ccccn2)n1] | ¹H NMR (400 MHz, DMSO) δ 11.49 (s, 1H), 9.91 (s, 1H), 8.62-8.36 (m, 1H), 7.86-7.77 (m, 3H), 7.77-7.69 (m, 1H), 7.41 (d, J = 8.8 Hz, 2H), 7.13 (d, J = 8.3 Hz, 1H), 6.97 (dd, J = 6.7, 5.4 Hz, 1H). ESI-MS m/z 408.0 [M + H]. |
| 69 | 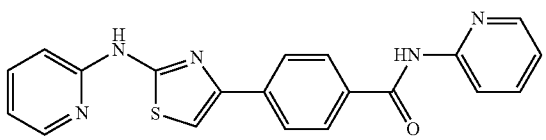 [SMILES: O=C(Nc1ccccn1)c1ccc(-c2csc(Nc3ccccn3)n2)cc1] | ¹H NMR (400 MHz, CDCl₃) δ 10.56 (s, 1H), 9.87 (s, 1H), 8.59 J = 8.4 Hz, 1H), 8.46-8.39 (m, 2H), 7.85 (t, J = 7.9 Hz, 1H), 7.69-7.58 (m, 5H), 7.20-7.14 (m, 1H), 7.05 (s, 1H), 6.95-6.91 (m, 1H), 6.87 (d, J = 8.2 Hz, 1H). ESI-MS m/z 374.4 [M + H]. |
| 70 | 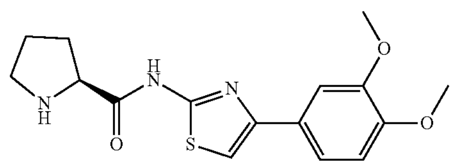 [SMILES: COc1ccc(-c2csc(NC(=O)[C@@H]3CCCN3)n2)cc1OC] | ESI-MS m/z 334.3 [M + H]. |
| 71 | 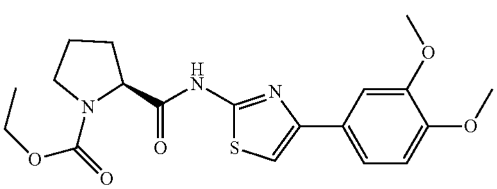 [SMILES: CCOC(=O)N1CCC[C@H]1C(=O)Nc1nc(-c2ccc(OC)c(OC)c2)cs1] | ESI-MS m/z 406.3 [M + H]. |
| 72 | 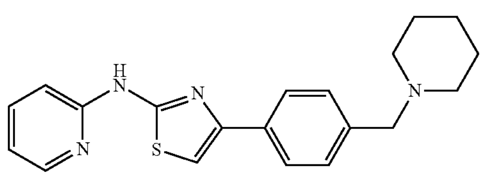 [SMILES: c1ccc(Nc2nc(-c3ccc(CN4CCCCC4)cc3)cs2)nc1] | ¹H NMR (400 MHz, DMSO-d₆) δ 11.40 (s, 1H), 8.31 (d, J = 4.0 Hz, 1H), 7.98 (d, J = 8.4Hz, 2H), 7.79-7.71 (m, 1H), 7.55 (d, J = 7.6 Hz, 2H), 7.52 (s, 1H), 7.11 (d, J = 8.4 Hz, 1H), 7.01-6.95 (m, 1H), 4.26 (s, 2H), 2.89 (s, 3H), 1.70-1.36 (m, 7H). ESI-MS m/z 351.5 [M + H]. |
| 73 | 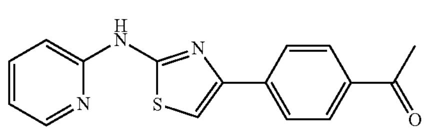 [SMILES: CC(=O)c1ccc(-c2csc(Nc3ccccn3)n2)cc1] | ¹H NMR (400 MHz, DMSO) δ 11.56 (s, 1H), 8.33 (d, J = 5.2 Hz, 1H), 8.06 (d, J = 8.4 Hz, 2H), 8.00 (t J = 8.0 Hz, 2H), 7.76 (t, J = 8.4 Hz, 1H), 7.68 (s, 1H), 7.13 (d, J = 8.4 Hz, 1H), 6.98 (t, J = 6.4 Hz, 1H), 2.60 (s, 3H). ESI-MS m/z 296.3 [M + H]. |
| 74 | 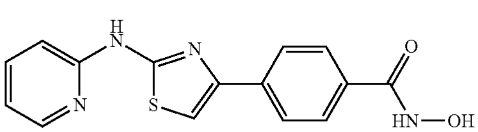 [SMILES: O=C(NO)c1ccc(-c2csc(Nc3ccccn3)n2)cc1] | ¹H NMR (400 MHz, DMSO) δ 11.43 (s, 1H), 11.22 (s, 1H), 9.01 (s, 1H), 8.31 (d, J = 4.1 Hz, 1H), 8.04-7.95 (m, 2H), 7.81 (d, J = 8.4 Hz, 2H), 7.72 (t, J = 7.8 Hz, 1H), 7.57 (s, 1H), 7.10 (d, J = 8.3 Hz, 1H), 6.97-6.91 (m, 1H). ESI-MS m/z 313.3 [M + H]. |

-continued

| No. | Structure | NMR/MS |
|---|---|---|
| 75 | 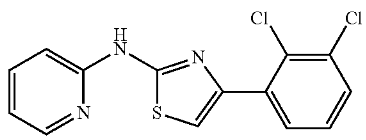 [SMILES: Clc1cccc(-c2csc(Nc3ccccn3)n2)c1Cl] | ¹H NMR (400 MHz, CDCl₃) δ 9.06 (s, 1H), 8.37 (d, J = 4.0 Hz, 1H), 7.97 (t, J = 17.5 Hz, 2H), 7.58-7.50 (m, 1H), 7.46 (dd, J = 10.1, 6.4 Hz, 3H), 7.25 (s, 2H), 7.10 (s, 1H), 6.88 (dd, J = 7.0, 5.2 Hz, 1H), 6.73 (d, J = 8.3 Hz, 1H). ESI-MS m/z 323.1 [M + H]. |
| 76 | 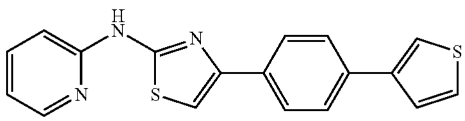 [SMILES: c1ccc(Nc2nc(-c3ccc(-c4ccsc4)cc3)cs2)nc1] | ¹H NMR (400 MHz, DMSO) δ 11.40 (s, 1H), 8.31 (d, J = 3.7 Hz, 1H), 7.95 (d, J = 8.3 Hz, 2H), 7.91 (dd, J = 2.7, 1.1 Hz, 1H), 7.78 (d, J = 8.3 Hz, 2H), 7.74-7.69 (m, 1H), 7.65 (dd, J = 5.0, 2.9 Hz, 1H), 7.61 (dd, J = 5.0, 1.0 Hz, 1H), 7.46 (s, 1H), 7.11 (d, J = 8.3 Hz, 1H), 6.93 (dd, J = 6.9, 5.3 Hz, 1H). ESI-MS m/z 336.4 [M + H]. |
| 77 | 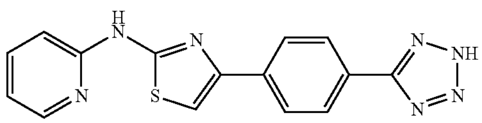 [SMILES: c1ccc(Nc2nc(-c3ccc(-c4nn[nH]n4)cc3)cs2)nc1] | ¹H NMR (400 MHz, DMSO) δ 11.48 (s, 1H), 8.32 (d, J = 4.5 Hz, 1H), 8.09 (d, J = 8.3 Hz, 2H), 7.88 (d, J = 8.3 Hz, 2H), 7.83-7.58 (m, 2H), 7.11 (d, J = 8.3 Hz, 1H), 7.00-6.82 (m, 1H). ESI-MS m/z 322.3 [M + H]. |
| 78 | 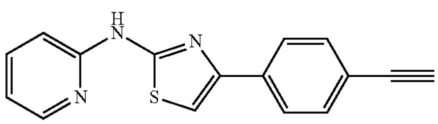 [SMILES: C#Cc1ccc(-c2csc(Nc3ccccn3)n2)cc1] | ¹H NMR (400 MHz, CDCl₃) δ 8.82 (s, 1H), 8.36 (d, J = 4.0 Hz, 1H), 7.83 (d, J = 8.3 Hz, 2H), 7.59-7.55 (m, 1H), 7.52 (d, J = 8.4 Hz, 2H), 7.07 (s, 1H), 6.89 (dd, J = 7.0, 5.2 Hz, 1H), 6.74 (d, J = 8.3 Hz, 1H), 3.12 (s, 1H). ESI-MS m/z 278.3 [M + H]. |
| 79 | 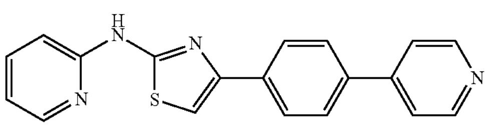 [SMILES: c1ccc(Nc2nc(-c3ccc(-c4ccncc4)cc3)cs2)nc1] | ¹H NMR (400 MHz, DMSO) δ 11.44 (s, 1H), 8.65 (d, J = 5.8 Hz, 2H), 8.33 (d, J = 4.7 Hz, 1H), 8.07 (d, J = 8.3 Hz, 2H), 7.90 (d, J = 8.3 Hz, 2H), 7.77 (d, J = 5.9 Hz, 2H), 7.73 (t, J = 7.8 Hz, 1H), 7.57 (s, 1H), 7.12 (d, J = 8.3 Hz, 1H), 6.99-6.91 (m, 1H). ESI-MS m/z 331.4 [M + H]. |
| 80 | 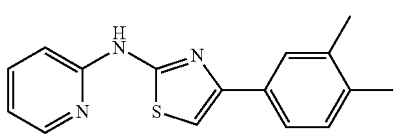 [SMILES: Cc1ccc(-c2csc(Nc3ccccn3)n2)cc1C] | ¹H NMR (400 MHz, DMSO) δ 11.63 (s, 1H), 8.35 (d, J = 5.0 Hz, 1H), 7.80 (s, 1H), 7.71 (s, 1H), 7.64 (d, J = 7.7 Hz, 1H), 7.38 (s, 1H), 7.17 (d, J = 7.2 Hz, 2H), 7.00 (d, J = 6.0 Hz, 1H), 2.27 (s, 3H), 2.24 (s, 3H). ESI-MS m/z 282.3 [M + H]. |
| 81 | 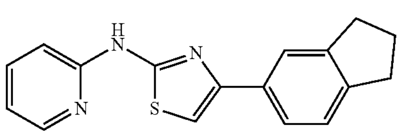 [SMILES: c1ccc(Nc2nc(-c3ccc4c(c3)CCC4)cs2)nc1] | ¹H NMR (400 MHz, DMSO) δ 11.63 (s, 1H), 8.35 (d, J = 5.0 Hz, 1H), 7.80 (s, 2H), 7.71 (s, 1H), 7.64 (d, J = 7.7 Hz, 1H), 7.38 (s, 1H), 7.26 (d, J = 8.0 Hz, 1H), 7.15 (d, J = 8.4 Hz, 1H), 6.98 (t, J = 6.0 Hz, 1H), 2.92-2.85 (m, 4H), 2.07-2.00 (m, 2H). ESI-MS m/z 294.3 [M + H]. |
| 82 | 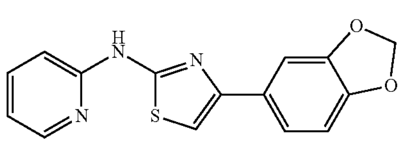 [SMILES: c1ccc(Nc2nc(-c3ccc4c(c3)OCO4)cs2)nc1] | ¹H NMR (400 MHz, DMSO) δ 11.67 (s, 1H), 8.36 (d, J = 4.9 Hz, 1H), 7.83 (t, J = 7.7 Hz, 1H), 7.48 (d, J = 8.0 Hz, 2H), 7.37 (s, 1H), 7.19 (d, J = 8.4 Hz, 1H), 7.02 (d, J = 6.0 Hz, 1H), |

| No. | Structure | NMR/MS |
|---|---|---|
| | | 6.97 (d, J = 7.9 Hz, 1H), 6.05 (s, 2H). ESI-MS m/z 298.3 [M + H]. |
| 83 | 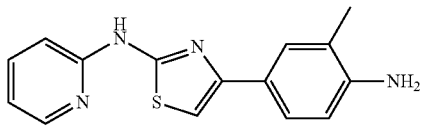 [SMILES: Cc1cc(-c2csc(Nc3ccccn3)n2)ccc1N] | ¹H NMR (400 MHz, DMSO) δ 11.28 (s, 1H), 8.28 (d, J = 4.5 Hz, 1H), 7.68 (t, J = 7.6 Hz, 1H), 7.51 (s, 1H), 7.45 (d, J = 8.2 Hz, 1H), 7.07 (d, J = 8.3 Hz, 1H), 6.99 (s, 1H), 6.90 (t, J = 5.6 Hz, 1H), 6.62 (d, J = 8.2 Hz, 1H), 4.97 (s, 2H), 2.10 (s, 3H). ESI-MS m/z 283.3 [M + H]. |

TEST EXAMPLE 1 UCP1 Luciferase Assay

Evaluating Compounds that Induce Ucp1 Up-Regulation

Ucp1-luciferase knock-in mice will be housed in cages and fed on standard chow diets (the detailed procedures please see reference 14). The 8-week-old mice will be killed by the cervical dislocation and put into 75% alcohol for 5 minutes. The inguinal adipose tissue will be dissected out and transferred to the three 10-cm petri dishes and washed with PBS for three times. The adipose tissue will be dissected and minced on a 10-cm petri dish for several minutes and then pipetted into 20 ml 0.1% collagenase solution in 50 ml conical tubes and digested at 37° C. for 1 hour. Next, 20 ml culture medium will be added to terminate the digestion and centrifuged for 10 minutes at 1000 rpm respectively. The supernatants will be removed and the pellets re-suspended in 10 mL culture medium and plated into 10-cm plates. The cells will be left to adhere to the plates overnight and the culture medium will be changed every other day. The confluent cells will be trypsinized, counted and plated to 24-well plate ($5 \times 10^4$ cells/well). The cells will be washed and re-fed the next day (as day −2). Two days later (day 0), the cells will usually become confluent and be induced to differentiate with MDIR medium. On day 2, the medium will be changed to IR medium and re-fed every 2 days. Complete differentiation is usually achieved by day 10. On day 10, the medium will be changed to the culture medium of 10% FBS/DMEM with indicated drugs along with the positive and negative controls for 2 days. The media will be removed and the cells washed with 1 ml PBS per well three times. Then 100 μl lysis buffer will be used to lyse the cells at 4° C. for 1 hour. 30 μl culture medium, 30 μl cell lysates and 60 μl Steady-Glo® Reagent were added to a well of 96-well-plate and the luminescence will be measured using a luminometer. The protein concentration will be determined using 20 μl cell lysates and specific activity of luciferase will be tabulated and data analyzed.

The bioactivity data of the compounds are listed in the following table.

| Compound No. | Ucp1 activation fold/corresponding concentration |
|---|---|
| 1 | 5.2/3 μM |
| 2 | 1.1/1 μM |
| 3 | 2.8/1 μM |
| 4 | 4.1/3 μM |
| 5 | 5.4/3 μM |
| 6 | 1.2/1 μM |
| 7 | 1.2/0.3 μM |
| 8 | 4.0/1 μM |
| 9 | 3.6/1 μM |
| 10 | 3.8/3 μM |
| 11 | 2.0/1 μM |
| 12 | 1.2/1 μM |
| 13 | 1.6/3 μM |
| 14 | 2.4/3 μM |
| 15 | 1.4/0.3 μM |
| 16 | 5.1/3 μM |
| 17 | 1.9/1 μM |
| 18 | 5.3/3 μM |
| 19 | 1.6/1 μM |
| 20 | 3.0/3 μM |
| 21 | 2.9/3 μM |
| 22 | 3.9/1 μM |
| 23 | 4.0/3 μM |
| 24 | 2.7/3 μM |
| 25 | 1.3/3 μM |
| 26 | 3.5/3 μM |
| 27 | 3.3/1 μM |
| 28 | 3.2/3 μM |
| 29 | 1.2/0.3 μM |
| 30 | 1.1/1 μM |
| 31 | 1.1/1 μM |
| 32 | 2.6/3 μM |
| 33 | 2.0/3 μM |
| 34 | 3.8/1 μM |
| 35 | 3.7/1 μM |
| 36 | 3.8/1 μM |
| 37 | 2.0/3 μM |
| 38 | 5.0/3 μM |
| 39 | 3.4/1 μM |
| 40 | 3.0/3 μM |
| 41 | 3.3/1 μM |
| 42 | 2.0/1 μM |
| 43 | 2.8/1 μM |
| 44 | 1.9/3 μM |
| 45 | 1.3/0.3 μM |
| 46 | 1.7/3 μM |
| 47 | 2.4/3 μM |
| 48 | 6.0/3 μM |
| 49 | 3.9/1 μM |
| 50 | 2.4/3 μM |
| 51 | 3.9/1 μM |
| 52 | 5.1/1 μM |
| 53 | 3.0/1 μM |
| 54 | 3.9/1 μM |
| 55 | 2.0/3 μM |
| 56 | 2.3/3 μM |
| 57 | 3.5/3 μM |
| 58 | 1.4/3 μM |
| 59 | 4.0/1 μM |
| 60 | 2.6/3 μM |
| 61 | 3.2/3 μM |

-continued

| Compound No. | Ucp1 activation fold/corresponding concentration |
|---|---|
| 62 | 2.2/3 μM |
| 63 | 5.9/3 μM |
| 64 | 1.1/1 μM |
| 65 | 1.1/3 μM |
| 66 | 1.0/3 μM |
| 67 | 3.1/3 μM |
| 68 | 1.3/3 μM |
| 69 | 4.6/3 μM |
| 70 | 1.7/0.3 μM |
| 71 | 1.7/0.3 μM |
| 72 | 1.8/3 μM |
| 73 | 1.2/3 μM |
| 74 | 3.0/3 μM |
| 75 | 1.1/3 μM |
| 76 | 1.8/3 μM |
| 77 | 1.1/3 μM |
| 78 | 2.3/1 μM |
| 79 | 1.8/3 μM |
| 80 | 1.5/3 μM |
| 81 | 2.0/1 μM |
| 82 | 2.4/1 μM |
| 83 | 6.0/3 μM |

TEST EXAMPLE 2

High Fat Diet Induced Obesity Mouse Model 8-week-old male mice (57BL/6J) were housed in metabolism cages and maintained on a 12 h lightdark cycle at 23° C. and fed high fat diet (HFD) (21.9 kJ/g, 60% of energy as fat, 20% of energy as protein, 20% of energy as carbohydrate; D12492; Research Diet, New Brunswick, N.J., USA) for 8 weeks. Then, diets induced obese mice were randomized into two groups according to glucose levels and body weight and gavaged with daily indicated drugs (50 mg/kg) or vehicle. Food intake and body weight was measured weekly. All experiments with animals were approved by the Animal Care and Use Committee of Guangzhou Institute of Biomedicine and Health, Chinese Academy of Sciences.

TEST EXAMPLE 3

Hematoxylin and Eosin Staining

Hematoxylin and eosin staining was performed as the standard protocol (see reference 15). As to the results, please see FIG. 1 (left panel) using compound 1 as the test compound.

TEST EXAMPLE 4

Immunochemistry

Wash sections in dH$_2$O three times for 5 minutes each. Incubate sections in 3% hydrogen peroxide for 10 minutes. Wash sections in dH$_2$O twice for 5 minutes each, and then wash sections in wash buffer for 5 minutes. Block each section with 100-400 μl blocking solution for 1 hour at room temperature. Remove blocking solution and add 100-400 μl primary UCP1 antibody to each section. Incubate overnight at 4° C. Remove antibody solution and wash sections in wash buffer three times for 5 minutes each. Add 100-400 μl biotinylated secondary antibodies, diluted in TBST to each section. Incubate 30 minutes at room temperature. Remove secondary antibody solution and wash sections three times with wash buffer for 5 minutes each. Add 100-400 μl DAB to each section and monitor staining closely. As soon as the sections develop, immerse slides in dH$_2$O. Wash sections in dH$_2$O two times for 5 minutes each. Incubate sections in 95% ethanol two times for 10 seconds each. Repeat in 100% ethanol, incubating sections two times for 10 seconds each. Repeat in xylene, incubating sections two times for 10 seconds each. Mount cover slips and take pictures. As to the results, please see FIG. 1 (right panel) using compound 1 as the test compound.

REFERENCES

1. Seale, P. & Lazar, M. A. Brown fat in humans: turning up the heat on obesity. *Diabetes* 58, 1482-1484, (2009).
2. Ishibashi, J. & Seale, P. Medicine. Beige can be slimming. *Science* 328, 1113-1114, (2010).
3. Wu, J., Bostrom, P., Sparks, L. M., Ye, L., Choi, J. H., Giang, A. H., Khandekar, M., Virtanen, K. A., Nuutila, P., Schaart, G., Huang, K., Tu, H., van Marken Lichtenbelt, W. D., Hoeks, J., Enerback, S., Schrauwen, P. & Spiegelman, B. M. Beige adipocytes are a distinct type of thermogenic fat cell in mouse and human. *Cell* 150, 366-376, (2012).
4. Petrovic, N., Walden, T. B., Shabalina, I. G., Timmons, J. A., Cannon, B. & Nedergaard, J. Chronic peroxisome proliferator-activated receptor gamma (PPARgamma) activation of epididymally derived white adipocyte cultures reveals a population of thermogenically competent, UCP1-containing adipocytes molecularly distinct from classic brown adipocytes. *J Biol Chem* 285, 7153-7164, (2010).
5. Schulz, T. J., Huang, P., Huang, T. L., Xue, R., McDougall, L. E., Townsend, K. L., Cypess, A. M., Mishina, Y., Gussoni, E. & Tseng, Y. H. Brown-fat paucity due to impaired BMP signalling induces compensatory browning of white fat. *Nature* 495, 379-383, (2013).
6. Mori, M., Nakagami, H., Rodriguez-Araujo, G., Nimura, K. & Kaneda, Y. Essential role for miR-196a in brown adipogenesis of white fat progenitor cells. *PLoS Biol* 10, e1001314, (2012).
7. Sharp, L. Z., Shinoda, K., Ohno, H., Scheel, D. W., Tomoda, E., Ruiz, L., Hu, H., Wang, L., Pavlova, Z., Gilsanz, V. & Kajimura, S. Human BAT possesses molecular signatures that resemble beige/brite cells. *PLoS One* 7, e49452, (2012).
8. Ohno, H., Shinoda, K., Spiegelman, B. M. & Kajimura, S. PPARgamma agonists induce a white-to-brown fat conversion through stabilization of PRDM16 protein. *Cell Metab* 15, 395-404, (2012).
9. Himms-Hagen, J., Melnyk, A., Zingaretti, M. C., Ceresi, E., Barbatelli, G. & Cinti, S. Multilocular fat cells in WAT of CL-316243-treated rats derive directly from white adipocytes. *Am J Physiol Cell Physiol* 279, C670-681, (2000).
10. Vegiopoulos, A., Muller-Decker, K., Strzoda, D., Schmitt, I., Chichelnitskiy, E., Ostertag, A., Berriel Diaz, M., Rozman, J., Hrabe de Angelis, M., Nusing, R. M., Meyer, C. W., Wahli, W., Klingenspor, M. & Herzig, S. Cyclooxygenase-2 controls energy homeostasis in mice by de novo recruitment of brown adipocytes. *Science* 328, 1158-1161, (2010).
11. Vila-Bedmar, R., Lorenzo, M. & Fernandez-Veledo, S. Adenosine 5'-monophosphate-activated protein kinase-mammalian target of rapamycin cross talk regulates brown adipocyte differentiation. *Endocrinology* 151, 980-992, (2010).

12. Tseng, Y. H., Kokkotou, E., Schulz, T. J., Huang, T. L., Winnay, J. N., Taniguchi, C. M., Tran, T. T., Suzuki, R., Espinoza, D. O., Yamamoto, Y., Ahrens, M. J., Dudley, A. T., Norris, A. W., Kulkarni, R. N. & Kahn, C. R. New role of bone morphogenetic protein 7 in brown adipogenesis and energy expenditure. *Nature* 454, 1000-1004, (2008).
13. Fisher, F. M., Kleiner, S., Douris, N., Fox, E. C., Mepani, R. J., Verdeguer, F., Wu, J., Kharitonenkov, A., Flier, J. S., Maratos-Flier, E. & Spiegelman, B. M. FGF21 regulates PGC-1 alpha and browning of white adipose tissues in adaptive thermogenesis. *Genes Dev* 26, 271-281, (2012).
14. Wu, D., Nie, T., Mao, L., Li, K., Tang, X., Li, P. and Xu, A. Non-human Mammalian Model with Knocked-in Uncoupling Protein-1-Luciferase Gene, method for constructing the same, and the application thereof. PCT/CN2014/092830 (2014).
15. Lillie R., Pizzolato P., Donaldson P. Nuclear stains with soluble metachrome mordant lake dyes. The effect of chemical endgroup blocking reactions and the artificial introduction of acid groups into tissues. Histochemistry 49: 23-35, (1976).

The invention claimed is:

1. A compound or physiologically acceptable salt or hydrate or solvate thereof, selected from the group consisting of:
1. 3-(2-(pyridin-2-ylamino)thiazol-4-yl)benzonitrile;
2. N-(4-(2-(pyridin-2-ylamino)thiazol-4-yl)phenyl)propionamide;
3. methyl 4-(2-(pyridin-2-ylamino)thiazol-4-yl)benzoate; and
4. 4-(4-amino-3-methylphenyl)-N-(pyridin-2-yl)thiazol-2-amine.

2. A pharmaceutical composition comprising the compound or physiologically acceptable salt or hydrate or solvate thereof of claim 1 and at least one pharmaceutically acceptable carrier or diluents.

3. The pharmaceutical composition of claim 2, wherein the composition is an oral composition, an injectable composition or a suppository.

* * * * *